United States Patent
Ichim et al.

(10) Patent No.: US 12,391,925 B2
(45) Date of Patent: Aug. 19, 2025

(54) PREVENTION AND/OR TREATMENT OF TYPE 1 DIABETES BY AUGMENTATION OF MYELOID SUPPRESSOR CELL ACTIVITY

(71) Applicant: CREATIVE MEDICAL TECHNOLOGIES, INC., Phoenix, AZ (US)

(72) Inventors: Thomas Ichim, San Diego, CA (US); Amit Patel, Salt Lake City, UT (US)

(73) Assignee: Creative Medical Technologies, Inc., Phoenix, AZ (US)

( * ) Notice: Subject to any disclaimer, the term of this patent is extended or adjusted under 35 U.S.C. 154(b) by 350 days.

(21) Appl. No.: 17/835,818

(22) Filed: Jun. 8, 2022

(65) Prior Publication Data

US 2022/0389385 A1    Dec. 8, 2022

Related U.S. Application Data

(60) Provisional application No. 63/208,249, filed on Jun. 8, 2021.

(51) Int. Cl.

| | | |
|---|---|---|
| *C12N 5/0775* | (2010.01) | |
| *A61K 40/10* | (2025.01) | |
| *A61K 40/22* | (2025.01) | |
| *A61K 40/41* | (2025.01) | |
| *A61L 27/38* | (2006.01) | |
| *A61P 3/10* | (2006.01) | |
| *C12N 5/078* | (2010.01) | |

(52) U.S. Cl.
CPC ............ *C12N 5/0662* (2013.01); *A61K 40/10* (2025.01); *A61K 40/22* (2025.01); *A61K 40/416* (2025.01); *A61L 27/3834* (2013.01); *A61P 3/10* (2018.01); *C12N 5/0634* (2013.01); *A61K 2239/31* (2023.05); *A61K 2239/38* (2023.05)

(58) Field of Classification Search
CPC .................................................. C12N 5/0622
See application file for complete search history.

(56) References Cited

PUBLICATIONS

Yin, Bingjiao, et al. "Myeloid-derived suppressor cells prevent type 1 diabetes in murine models." The Journal of Immunology 185.10 (2010): 5828-5834 (Year: 2010).*

Giganti, Giulio, et al. "Treg cell therapy: How cell heterogeneity can make the difference." European Journal of Immunology 51.1 (published: Dec. 4, 2020): 39-55. (Year: 2020).*

Veglia, Filippo, Emilio Sanseviero, and Dmitry I. Gabrilovich. "Myeloid-derived suppressor cells in the era of increasing myeloid cell diversity." Nature Reviews Immunology 21.8 (Published: Feb, 1, 2021): 485-498 (Year: 2021).*

Do, Jeong-su, et al. "Mesenchymal stromal cell mitochondrial transfer to human induced T-regulatory cells mediates FOXP3 stability." Scientific reports 11.1 (published: May 21, 2021): 10676. (Year: 2021).*

Zhao, Yong, et al. "Human cord blood stem cell-modulated regulatory T lymphocytes reverse the autoimmune-caused type 1 diabetes in nonobese diabetic (NOD) mice." PloS one 4.1 (2009): e4226. (Year: 2009).*

Bluestone, Jeffrey A., et al. "Type 1 diabetes immunotherapy using polyclonal regulatory T cells." Science translational medicine 7.315 (2015): 315ra189-315ra189. (Year: 2015).*

D'Aveni, Maud, et al. "Myeloid-derived suppressor cells in the context of allogeneic hematopoietic stem cell transplantation." Frontiers in immunology 11 (2020): 989. (Year: 2020).*

* cited by examiner

*Primary Examiner* — Christopher M Babic
*Assistant Examiner* — Brendan Thomas Tinsley
(74) *Attorney, Agent, or Firm* — Baumgartner Patent Land, LLC; Marc Baumgartner

(57) ABSTRACT

Disclosed are means, methods and compositions of matter useful for prevention and/or reversion of type 1 diabetes by upregulation of myeloid suppressor cell activity in a mammal suffering from and/or at risk of developing type 1 diabetes. In one embodiment the invention teaches administration of immune cells that have been conditioned by exposure to regenerative cells, and/or cultured in the presence of factors produced from regenerative cells. In one embodiment said regenerative cells are umbilical cord derived mesenchymal stem cells. In one embodiment, immune cells that have been exposed to said regenerative cells are administered together with agents known to enhance myeloid suppressor cell activity. In another embodiment immune cells are administered together with exogenous myeloid suppressor cells.

14 Claims, 1 Drawing Sheet

PREVENTION AND/OR TREATMENT OF TYPE 1 DIABETES BY AUGMENTATION OF MYELOID SUPPRESSOR CELL ACTIVITY

CROSS-REFERENCE TO RELATED APPLICATIONS

This application claims priority to U.S. Provisional Application Ser. No. 63/208,249, filed on Jun. 8, 2021, which is incorporated by reference in its entirety.

FIELD OF THE INVENTION

The invention belongs to the field of diabetes more specifically the invention belongs to the field of treating or preventing Type 1 diabetes by utilizing modulated immune cells.

BACKGROUND OF THE INVENTION

Diabetes is a severe medical condition that effects millions of people. There is a need in the art for improved methods of treating and preventing this disease.

SUMMARY

Preferred embodiments are directed to methods of prevention, ameliorating or reversing type 1 diabetes comprising the steps of: a) selecting a patient in need of treatment; b) extracting an immune cell population from said patient; c) culturing said immune cell population with a regenerative cell population or exposing said immune cell population to said conditioned media from said regenerative cell population; d) administering said immune cell population back to said patient in need of treatment; e) administering prior to and/or concurrent with, and/or subsequent to said immune cell population agents capable of enhancing number and/or activity of myeloid suppressor cells; and f) optionally administering prior to and/or concurrent with, and/or subsequent to said immune cell population a population of exogenous myeloid suppressor cells.

Preferred methods include embodiments wherein said type 1 diabetes is immunologically mediated pathology of the pancreas.

Preferred methods include embodiments wherein said type 1 diabetes is a portion or a whole of the pancreatic islets being destroyed or impaired by immunologically mediated attack.

Preferred methods include embodiments wherein said type 1 diabetes is a portion or a whole of the pancreatic islets being destroyed or impaired by inappropriate cell death.

Preferred methods include embodiments wherein said inappropriate cell death is apoptosis.

Preferred methods include embodiments wherein said inappropriate cell death is necrosis.

Preferred methods include embodiments wherein said inappropriate cell death is ferroptosis.

Preferred methods include embodiments wherein said inappropriate cell death is necroptosis.

Preferred methods include embodiments wherein said diabetes is inflammation of the pancreas.

Preferred methods include embodiments wherein said diabetes is pancreatitis.

Preferred methods include embodiments wherein said diabetes is infiltration of the pancreas by T cells.

Preferred methods include embodiments wherein said diabetes is infiltration of the pancreas by dendritic cells.

Preferred methods include embodiments wherein said diabetes is infiltration of the pancreas by B cells.

Preferred methods include embodiments wherein said diabetes is infiltration of the pancreas by cytotoxic T cells.

Preferred methods include embodiments wherein said diabetes is infiltration of the pancreas by NK cells Preferred methods include embodiments wherein said diabetes is infiltration of the pancreas by NKT cells Preferred methods include embodiments wherein said diabetes is infiltration of the pancreas by gamma delta T cells Preferred methods include embodiments wherein said diabetes is associated with a viral infection.

Preferred methods include embodiments wherein said viral infection is an enteroviral infection.

Preferred methods include embodiments wherein said viral infection augments interferon alpha production.

Preferred methods include embodiments wherein said viral infection is a coxsackie viral infection.

Preferred methods include embodiments wherein said immune cells are extracted from a patient who is not the recipient.

Preferred methods include embodiments wherein said immune cells are xenogeneic.

Preferred methods include embodiments wherein said immune cells are cord blood derived.

Preferred methods include embodiments wherein said immune cells are derived from pluripotent stem cells.

Preferred methods include embodiments wherein said immune cells are cultured together with said regenerative cells in the presence of an activator of an immune receptor.

Preferred methods include embodiments wherein said immune receptor activates immunotyrosine activation motifs.

Preferred methods include embodiments wherein said immune receptor activates NF-AT.

Preferred methods include embodiments wherein said immune receptor activates NF-kappa B.

Preferred methods include embodiments wherein said immune receptor activates STAT-3.

Preferred methods include embodiments wherein said immune receptor activates STAT-4.

Preferred methods include embodiments wherein said immune receptor activates janus activated kinase.

Preferred methods include embodiments wherein said immune receptor activates MAP-kinase.

Preferred methods include embodiments wherein said immune receptor is TLR. 1

Preferred methods include embodiments wherein said TLR-1 is activated by Pam3CSK4.

Preferred methods include embodiments wherein said immune receptor is TLR-2

Preferred methods include embodiments wherein said TLR-2 is activated by HKLM.

Preferred methods include embodiments wherein said immune receptor is TLR-3.

Preferred methods include embodiments wherein said TLR-3 is activated by Poly:IC.

Preferred methods include embodiments wherein said immune receptor is TLR-4.

Preferred methods include embodiments wherein said TLR-4 is activated by LPS.

Preferred methods include embodiments wherein said TLR-4 is activated by B uprenorphine.

Preferred methods include embodiments wherein said TLR-4 is activated by Carbamazepine.

Preferred methods include embodiments wherein said TLR-4 is activated by Fentanyl.

Preferred methods include embodiments wherein said TLR-4 is activated by Levorphanol.

Preferred methods include embodiments wherein said TLR-4 is activated by Methadone.

Preferred methods include embodiments wherein said TLR-4 is activated by Cocaine.

Preferred methods include embodiments wherein said TLR-4 is activated by Morphine.

Preferred methods include embodiments wherein said TLR-4 is activated by Oxcarbazepine.

Preferred methods include embodiments wherein said TLR-4 is activated by Oxycodone.

Preferred methods include embodiments wherein said TLR-4 is activated by Pethidine.

Preferred methods include embodiments wherein said TLR-4 is activated by Glucuronoxylomannan from *Cryptococcus*.

Preferred methods include embodiments wherein said TLR-4 is activated by Morphine-3-glucuronide.

Preferred methods include embodiments wherein said TLR-4 is activated by lipoteichoic acid.

Preferred methods include embodiments wherein said TLR-4 is activated by beta.-defensin 2.

Preferred methods include embodiments wherein said TLR-4 is activated by low molecular weight hyaluronic acid.

Preferred methods include embodiments wherein said low molecular weight hyaluronic acid has a molecular weight of <1000 kDa.

Preferred methods include embodiments wherein said low molecular weight hyaluronic acid has a molecular weight of <500 kDa.

Preferred methods include embodiments wherein said low molecular weight hyaluronic acid has a molecular weight of <250 kDa.

Preferred methods include embodiments wherein said low molecular weight hyaluronic acid has a molecular weight of <100 kDa.

Preferred methods include embodiments wherein said TLR-4 is activated by fibronectin EDA.

Preferred methods include embodiments wherein said TLR-4 is activated by snapin.

Preferred methods include embodiments wherein said TLR-4 is activated by tenascin C.

Preferred methods include embodiments wherein said immune receptor is TLR-5.

Preferred methods include embodiments wherein said TLR-5 is activated by flaggelin.

Preferred methods include embodiments wherein said immune receptor is TLR-6.

Preferred methods include embodiments wherein said TLR-6 is activated by FSL-1.

Preferred methods include embodiments wherein said immune receptor is TLR-7.

Preferred methods include embodiments wherein said TLR-7 is activated by imiquimod.

Preferred methods include embodiments wherein said immune receptor is TLR-8.

Preferred methods include embodiments wherein said TLR-8 is activated by ssRNA40/LyoVec.

Preferred methods include embodiments wherein said immune receptor is TLR-9.

Preferred methods include embodiments wherein said TLR-9 is activated by a CpG oligonucleotide.

Preferred methods include embodiments wherein said TLR-9 is activated by ODN2006.

Preferred methods include embodiments wherein said TLR-9 is activated by Agatolimod.

Preferred methods include embodiments wherein said TLR-9 is activated by ODN2007.

Preferred methods include embodiments wherein said TLR-9 is activated by ODN1668.

Preferred methods include embodiments wherein said TLR-9 is activated by ODN1826.

Preferred methods include embodiments, wherein said TLR-9 is activated by ODN BW006.

Preferred methods include embodiments wherein said TLR-9 is activated by ODN D SL01.

Preferred methods include embodiments wherein said TLR-9 is activated by ODN 2395.

Preferred methods include embodiments wherein said TLR-9 is activated by ODN M362.

Preferred methods include embodiments wherein said TLR-9 is activated by ODN SL03.

Preferred methods include embodiments wherein said regenerative cell is a stem cell.

Preferred methods include embodiments wherein said stem cell is a hematopoietic stem cell.

Preferred methods include embodiments wherein said hematopoietic stem cell is capable of generating leukocytic, lymphocytic, thrombocytic and erythrocytic cells when transplanted into an immunodeficient animal.

Preferred methods include embodiments wherein said hematopoietic stem cell is non-adherent to plastic.

Preferred methods include embodiments wherein said hematopoietic stem cell is adherent to plastic.

Preferred methods include embodiments wherein said hematopoietic stem cell is exposed to hyperthermia.

Preferred methods include embodiments wherein said hematopoietic stem cell expresses interleukin-3 receptor.

Preferred methods include embodiments wherein said hematopoietic stem cell expresses interleukin-1 receptor.

Preferred methods include embodiments wherein said hematopoietic stem cell expresses c-met.

Preferred methods include embodiments wherein said hematopoietic stem cell expresses mpl.

Preferred methods include embodiments wherein said hematopoietic stem cell expresses interleukin-11 receptor.

Preferred methods include embodiments wherein said hematopoietic stem cell expresses G-CSF receptor.

Preferred methods include embodiments wherein said hematopoietic stem cell expresses GM-CSF receptor.

Preferred methods include embodiments wherein said hematopoietic stem cell expresses M-CSF receptor.

Preferred methods include embodiments wherein said hematopoietic stem cell expresses VEGF-receptor.

Preferred methods include embodiments wherein said hematopoietic stem cell expresses c-kit.

Preferred methods include embodiments wherein said hematopoietic stem cell expresses CD33.

Preferred methods include embodiments wherein said hematopoietic stem cell expresses CD133.

Preferred methods include embodiments wherein said hematopoietic stem cell expresses CD34.

Preferred methods include embodiments wherein said hematopoietic stem cell expresses Fas ligand.

Preferred methods include embodiments wherein said hematopoietic stem cell does not express lineage markers.

Preferred methods include embodiments wherein said hematopoietic stem cell does not express CD14.

Preferred methods include embodiments wherein said hematopoietic stem cell does not express CD16.

Preferred methods include embodiments wherein said hematopoietic stem cell does not express CD3.

Preferred methods include embodiments wherein said hematopoietic stem cell does not express CD56.

Preferred methods include embodiments wherein said hematopoietic stem cell does not express CD38.

v wherein said hematopoietic stem cell does not express CD30.

Preferred methods include embodiments wherein said regenerative cell is a mesenchymal stem cell.

Preferred methods include embodiments wherein said mesenchymal stem cells are naturally occurring mesenchymal stem cells.

Preferred methods include embodiments wherein said mesenchymal stem cells are generated in vitro.

Preferred methods include embodiments wherein said naturally occurring mesenchymal stem cells are tissue derived.

Preferred methods include embodiments wherein said naturally occurring mesenchymal stem cells are derived from a bodily fluid.

Preferred methods include embodiments wherein said tissue derived mesenchymal stem cells are selected from a group comprising of: a) bone marrow; b) perivascular tissue; c) adipose tissue; d) placental tissue; e) amniotic membrane; f) omentum; g) tooth; h) umbilical cord tissue; i) fallopian tube tissue; j) hepatic tissue; k) renal tissue; 1) cardiac tissue; m) tonsillar tissue; n) testicular tissue; o) ovarian tissue; p) neuronal tissue; q) auricular tissue; r) colonic tissue; s) submucosal tissue; t) hair follicle tissue; u) pancreatic tissue; v) skeletal muscle tissue; and w) subepithelial umbilical cord tissue.

Preferred methods include embodiments wherein said tissue derived mesenchymal stem cells are isolated from tissues containing cells selected from a group of cells comprising of: endothelial cells, epithelial cells, dermal cells, endodermal cells, mesodermal cells, fibroblasts, osteocytes, chondrocytes, natural killer cells, dendritic cells, hepatic cells, pancreatic cells, stromal cells, salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epididymal principal cells, epididymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

Preferred methods include embodiments wherein said mesenchymal stem cells are plastic adherent.

Preferred methods include embodiments wherein said mesenchymal stem cells express a marker selected from a group comprising of: a) CD73; b) CD90; and c) CD105.

Preferred methods include embodiments wherein said mesenchymal stem cells lack expression of a marker selected from a group comprising of: a) CD14; b) CD45; and c) CD34.

Preferred methods include embodiments wherein said mesenchymal stem cells from umbilical cord tissue express markers selected from a group comprising of; a) oxidized low density lipoprotein receptor 1, b) chemokine receptor ligand 3; and c) granulocyte chemotactic protein.

Preferred methods include embodiments wherein said mesenchymal stem cells from umbilical cord tissue do not express markers selected from a group comprising of: a) CD117; b) CD31; c) CD34; and CD45;

Preferred methods include embodiments wherein said mesenchymal stem cells from umbilical cord tissue express, relative to a human fibroblast, increased levels of interleukin 8 and reticulon 1

Preferred methods include embodiments wherein said mesenchymal stem cells from umbilical cord tissue have the potential to differentiate into cells of at least a skeletal muscle, vascular smooth muscle, pericyte or vascular endothelium phenotype.

v wherein said mesenchymal stem cells from umbilical cord tissue express markers selected from a group comprising of: a) CD10; b) CD13; c) CD44; d) CD73; and e) CD90.

Preferred methods include embodiments wherein said umbilical cord tissue mesenchymal stem cell is an isolated umbilical cord tissue cell isolated from umbilical cord tissue substantially free of blood that is capable of self-renewal and expansion in culture, Preferred methods include embodiments wherein said umbilical cord tissue mesenchymal stem cells has the potential to differentiate into cells of other phenotypes.

Preferred methods include embodiments wherein said other phenotypes comprise: a) osteocytic; b) adipogenic; and c) chondrogenic differentiation.

Preferred methods include embodiments wherein said cord tissue derived mesenchymal stem cells can undergo at least 20 doublings in culture.

Preferred methods include embodiments wherein said cord tissue derived mesenchymal stem cell maintains a normal karyotype upon passaging Preferred methods include embodiments wherein said cord tissue derived mesenchymal stem cell expresses a marker selected from a group of markers comprised of: a) CD10 b) CD13; c) CD44; d) CD73; e) CD90; f) PDGFr-alpha; g) PD-L2; and h) HLA-A,B,C v wherein said cord tissue mesenchymal stem cells does not express one or more markers selected from a group comprising of; a) CD31; b) CD34; c) CD45; d) CD80; e) CD86; f) CD117; g) CD141; h) CD178; i) B7-H2; j) HLA-G and k) HLA-DR,DP,DQ.

Preferred methods include embodiments wherein said umbilical cord tissue-derived cell secretes factors selected from a group comprising of: a) MCP-1; b) MIP1beta; c) IL-6; d) IL-8; e) GCP-2; f) HGF; g) KGF; h) FGF; i) HB-EGF; j) BDNF; k) TPO;1) RANTES; and m) TIMP1

Preferred methods include embodiments wherein said umbilical cord tissue derived cells express markers selected from a group comprising of: a) TRA1-60; b) TRA1-81; c) SSEA3; d) SSEA4; and e) NANOG.

Preferred methods include embodiments wherein said umbilical cord tissue-derived cells are positive for alkaline phosphatase staining.

DESCRIPTION OF THE INVENTION

Figure 1:
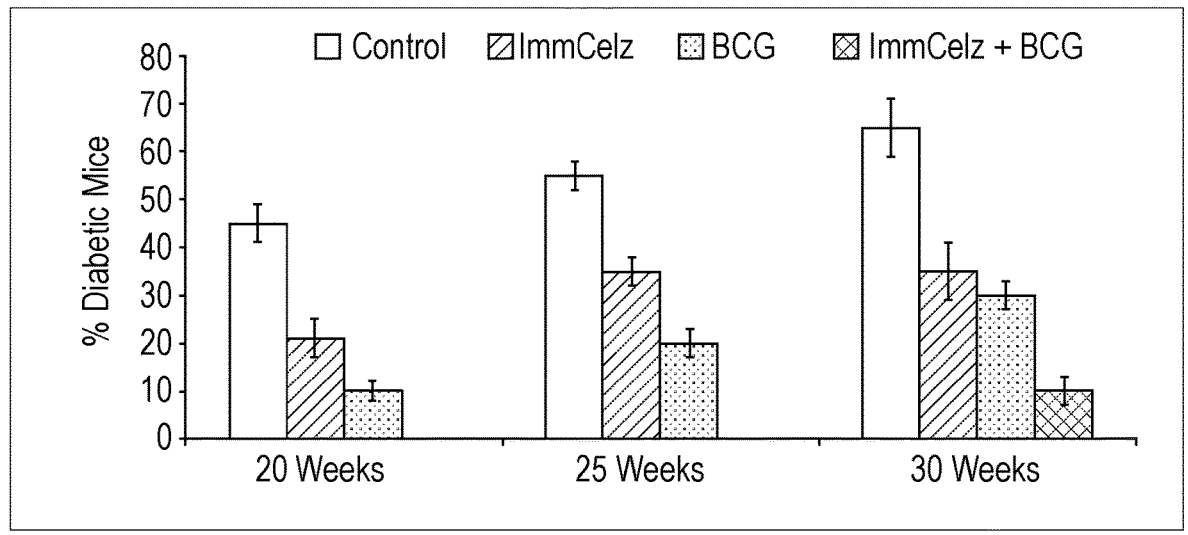
FIG. 1 is a bar graph showing the effects of BCG and IMMCELZ™ on diabetic mice.

In one embodiment the invention provides leveraging the immune regulatory properties of myeloid derived suppressor cells to inhibit diabetes progression as a synergistic approach to addition of immune regulatory cells endowed with regenerative capacity by coculture or exposure to products generated by said regenerative cells.

"Adaptive immunity" is described as T and B cell immune responses work together with innate immune responses. The basis of the adaptive immune response is that of clonal recognition and response. An antigen selects the clones of cell which recognize it, and the first element of a specific immune response must be rapid proliferation of the specific lymphocytes. This is followed by further differentiation of the responding cells as the effector phase of the immune response develops. In T-cell mediated non-infective inflammatory diseases and conditions, immunosuppressive drugs inhibit T-cell proliferation and block their differentiation and effector functions.

"T cell response" means an immunological response involving T cells. The T cells that are "activated" divide to produce memory T cells or cytotoxic T cells. The cytotoxic T cells bind to and destroy cells recognized as containing the antigen. The memory T cells are activated by the antigen and thus provide a response to an antigen already encountered. This overall response to the antigen is the T cell response.

"autoimmune disease" or "autoimmune response" is a response in which the immune system of an individual initiates and may propagate a primary and/or secondary response against its own tissues or cells. An "alloimmune response" is one in which the immune system of an individual initiates and may propagate a primary and/or secondary response against the tissues, cells, or molecules of another, as, for example, in a transplant or transfusion.

The term "cell-mediated immunity" refers to (1) the recognition and/or killing of virus and virus-infected cells by leukocytes and (2) the production of different soluble factors (cytokines) by these cells when stimulated by virus or virus-infected cells. Cytotoxic T lymphocytes (CTLs), natural killer (NK) cells and antiviral macrophages are leukocytes that can recognize and kill virus-infected cells. Helper T cells can recognize virus-infected cells and produce a number of important cytokines. Cytokines produced by monocytes (monokines), T cells, and NK cells (lymphokines) play important roles in regulating immune functions and developing antiviral immune functions. A host T cell response can be directed against cells of the host, as in autoimmune disease. For example, the T cells in type I diabetes (T1D) recognize an "antigen" that is expressed by the host, which causes the destruction of normal host cells—for T1D, the endocrine cells of the islets of Langerhans of the pancreas. A T cell response may also occur within a host that has received a graft of foreign cells, as is the case in graft-versus-host disease (GVHD) in which T cells from the graft attack the cells of the host, or in the case of graft rejection in which T cells of the host attack the graft.

"T regulatory cell" or "Treg cell" or "Tr cell" refers to a cell that can inhibit a T cell response [1-5]. Treg cells express the transcription factor Foxp3, which is not upregulated upon T cell activation and discriminates Tregs from activated effector cells [6]. Tregs are identified by the cell surface markers CD25, CD45RB, CTLA4, and GITR. Treg development is induced by MDSC activity [7]. Several Treg subsets have been identified that have the ability to inhibit autoimmune and chronic inflammatory responses and to maintain immune tolerance in tumor-bearing hosts [8]. These subsets include interleukin 10-(IL-10-) secreting T regulatory type 1 (Tr1) cells, transforming growth factor-.beta.-(TGF-.beta.-) secreting T helper type 3 (Th3) cells, and "natural" CD4.sup.+/CD25.sup.+ Tregs (Trn).

The phrase "inducing T regulatory cells" means activation, amplification, and generation of Tregs to inhibit or reduce the T cell response. One method of induction is through the use of the MDSCs.

The phrase "T cell tolerance" refers to the anergy (non-responsiveness) of T cells when presented with an antigen. T cell tolerance prevents a T cell response even in the presence of an antigen that existing memory T cells recognize.

"Differentiate" refers to the genetic process by which cells are produced with a specialized phenotype. A differentiated cell of any type has attained all of the characteristics that define that cell type. This is true even in the progression of cell types. For example, if cell type X matures to cell type Y which then overall matures to cell type Z, an X cell differentiates to a Y cell when it has attained all of the characteristics that define a type Y cell, even though the cell has not completely differentiated into a type Z cell.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as V.sub.H) and a heavy chain constant region. The heavy chain constant region is comprised of three domains, C.sub.H1, C.sub.H2 and C.sub.H3. Each light chain is comprised of a light chain variable region (abbreviated herein as V.sub.L) and a light chain constant region. The light chain constant region is comprised of one domain, C.sub.L. The V.sub.H and V.sub.L regions can be further subdivided into regions of hypervariability, termed complementarity determining regions (CDR), interspersed with regions that are more conserved, termed framework regions (FR). Each V.sub.H and V.sub.L is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

"Cytokine" is a generic term for a group of proteins released by one cell population which act on another cell population as intercellular mediators. Examples of such cytokines are lymphokines, monokines, and traditional polypeptide hormones. Included among the cytokines are interferons (IFN, notably IFN-.gamma.), interleukins (IL, notably IL-1, IL-2, IL-4, IL-10, IL-12), colony stimulating factors (CSF), macrophage colony stimulating factor (M-CSF), granulocyte macrophage colony stimulating factor (GM-CSF), thrombopoietin (TPO), erythropoietin (EPO), leukemia inhibitory factor (LIF), kit-ligand, growth hormones (GH), insulin-like growth factors (IGF), parathyroid hormone, thyroxine, insulin, relaxin, follicle stimulating hormone (FSH), thyroid stimulating hormone (TSH), leutinizing hormone (LH), hematopoietic growth factor, hepatic growth factor, fibroblast growth factors (FGF), prolactin, placental lactogen, tumor necrosis factors (TNF), mullerian-inhibiting substance, mouse gonadotropin-associated peptide, inhibin, activin, vascular endothelial growth factor (VEGF), integrin, nerve growth factors (NGF), platelet growth factor, transforming growth factors (TGF), osteoinductive factors, etc. Those of particular interest for the present invention include IFN-.gamma., IL-10, and TGF-.beta.

"Autoantigen" refers to a molecule that is endogenous to a cell or organism that induces an autoimmune response.

"Transplant rejection" means that a transplant of tissue or cells is not tolerated by a host individual. The transplant is not tolerated in that it is attacked by the host's own immune system or is otherwise not supported by the host. The transplant may be an allotransplant, a transplant of tissue or cells from another individual of the same species, or an autotransplant, a transplant of the host's own tissue or cells. Transplant rejection encompasses the rejection of fluids through transfusion.

The term "subject" or "individual" as used herein refers to an animal having an immune system, preferably a mammal (e.g., rodent such as mouse). In particular, the term refers to humans.

The immune suppressive properties of myeloid derived suppressor cells have been well described in the literature and one of skill in the art is referred to various relevant publication for better understanding and practice of the invention. Myeloid derived suppressor cells have been implicated in tuberculosis infection [9, 10], cancer [11-28], transplantation tolerance [29-35], graft versus host disease [36].

Manipulation of myeloid derived suppressor cell activity has been previously used therapeutically in that suppression of their activity by agents such as PDE5 inhibitors [37], all-trans-retinoic acid [38], amino-bisphosphonates [39], stat 3 inhibitors [40], triterpenoids [10, 41], 5-flourouracil [42], cox-2 inhibitors [43], have been used for immune stimulation. In contrast, the current invention teaches means of enhancing myeloid derived suppressor activity in order to induce immunological tolerance to diabetogenic antigens and/or to protect pancreatic islet cells from death. In some embodiments the invention uses patient lymphocytes conditioned by stem cells to increase TGF-beta expression on myeloid suppressor cells, thereby increasing potency of myeloid suppressor cell inhibition of immunity [44]. In some embodiments of the invention activation of IL-4 receptor myeloid derived suppressor cells [45], is disclosed through administration of patient lymphocytes that have been conditioned with regenerative cells.

In one embodiment of the invention, compounds that stimulate activity of myeloid derived suppressor cells are given along with the regenerative cell reprogrammed PBMC. In one embodiment compounds such as interleukin-6 [46-49], PGE-2 [50], S100A9 [51], exosomes [52, 53], LPS and interferon gamma [54], GM-CSF [55, 56], IL-6 [57], M-CSF [58], BCG [59], alcohol consumption [60], TLR-2 activators [61], hepatic acute phase proteins such as serum amyloid A and Cxcl1/K [62], Galectin-9 [63], anti-CD137 antibodies [57] re administered to augment activity of myeloid derived suppressor cells. In some embodiments, enhancement of myeloid derived suppressor cell function such as increasing arginine metabolism [64], is accomplished by activation of said cells with agent such as toll like receptor activators.

In one embodiment of the invention, IL-17 producing gamma delta T cells are utilized to generate myeloid suppressor cells which can be used in the context of the invention to prevent or reverse diabetes. The utilization of IL-17 producing gamma delta T cells to generate myeloid suppressor cells is described [65-69]. Additionally, simple IL-17 administration either directly, or through administration of cells secreting IL-17 may be used for stimulation of myeloid derived suppressor cells [70, 71]. In some embodiments of the invention, myeloid derived suppressor cells are utilized to kill NK cells [72], wherein said ex vivo conditioned patient lymphocytes are utilized to enhance ability of myeloid suppressor cells to kill NK cells.

In some embodiments patient immune cells conditioned by mesenchymal stem cells are utilized to enhance angiogenic activity of myeloid derived suppressor cells [73]. Stimulation of angiogenesis may be utilized to enhance engraftment of allogeneic pancreatic transplants. In some embodiments the ability of myeloid derived suppressor cells to deplete cystine and/or cysteine [74], is augmented by exposure to patient lymphocytes that have been conditioned by regenerative cells.

In one embodiment, the invention provides for a method of making an autologous immunological composition for the treatment of diabetes in humans, comprising: providing a peripheral blood composition from a human patient in need of treatment, extracting CD3.sup.+ T cells, in which the CD3.sup.+ T cells are enriched for T cells reactive to antigens uniquely expressed by the pancreatic islets and subsequently inducing said CD3 T cells to possess a tolerogenic and/or regenerative phenotype through incubation with a mesenchymal stem cell population. In some embodiments, the antigens found on pancreatic islet cells are proteins or peptides. These antigens may be identified by whole exome sequencing and RNAseq of pancreatic, beta cell, and alpha cell tissues the same individual, and HLA binding algorithms applied to determine which pancreatic beta cell specific peptides bind HLA molecules.

In some embodiments, the recipient has been immunized against pancreatic beta cell specific antigens prior to extraction of T cells for reprogramming with mesenchymal stem cells. The practice of inducing a tolerogenic vaccine to diabetes has been previously described. In one embodiment preimmunization with pancreatic associated peptides can be performed as described by others and incorporated by reference [75-105]. In some cases, immunization with GAD peptide may be performed intralymphatically in order to induce a more tolerogenic response [106, 107]. Enhancement of tolerogenicity may be achieved by administration of various supplements such as vitamin D [108], or cytokine blocking agents [109]. Because vaccination with diabetic autoantigens has been previously shown to induce T regulatory cells [110], in some embodiments of the invention, T regulatory cells are assessed in response to vaccination and if needed, additional vaccines and/or tolerogenic interventions may be performed before extract patient cells for tolerogenic reprogramming.

In some embodiments, the immunization consists of intramuscular injection of antigen emulsified in an adjuvant, DNA vaccination plus electroporation, etc.

In one embodiment of the invention, administration of PGE-2, or agents or cells that induce expression of PGE2 is performed in order to increase activity and/or numbers of myeloid derived suppressor cells. Means of administration of PGE-2 can be borrowed from publications which describe induction of myeloid suppressor cells by tumor associated PGE-2 [111]. In another embodiment VEGF is administered to induce augmentation of activity and/or number of myeloid derived suppressor cells [112]. In another embodiment low dose interleukin-2 is administered as a means of augmenting myeloid derived suppressor cell number and/or activity [113].

In one embodiment immunization means are utilized before extraction of patient immune cells for reprogramming by regenerative cells. The patient's T cells, which possess CD3+ are made toleroenic and reactive to one or more pancreatic antigens.

In some embodiments of the invention, prior to expansion, a source of T cells is obtained from a subject. The term "subject" is intended to include living organisms in which an immune response can be elicited (e.g., mammals). Examples of subjects include humans, dogs, cats, mice, rats, and transgenic species thereof. In some embodiments, the subject is a partially or fully HLA-matched healthy donor (i.e., non-cancerous donor). T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media. In another embodiment, T cells are isolated from peripheral blood lymphocytes by lysing the red blood cells and depleting the monocytes, for example, by centrifugation through a PERCOLL.TM. gradient or by counterflow centrifugal elutriation. A specific subpopulation of T cells, such as CD3.sup.+, CD28.sup.+, CD4.sup.+, CD8.sup.+, CD45RA.sup.+, and CD45RO.sup.+ T cells, can be further isolated by positive or negative selection techniques. For example, in some embodiment, T cells are isolated by incubation with anti-CD3/anti-CD28 (i.e., 3.times.28)-conjugated beads, such as DYNABEADS™, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells. Further, use of longer incubation times can increase the efficiency of capture of T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

In one embodiment, enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, or from samples where there are many tumor cells present (i.e., leukemic blood, tumor tissue, etc.). Such populations of cells may have therapeutic value and would be desirable to obtain. In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10.degree. C. or at room temperature. If desired or necessary, T cell populations (i.e., $CD3^+$ cells) may be depleted from blood preparations prior to ex vivo expansion by a variety of methodologies, including anti-CD3 coated beads or columns, or utilization of the phagocytotic activity of these cells to facilitate removal, or by the use of counterflow centrifugal elutriation. Accordingly, in one embodiment, the invention uses paramagnetic particles of a size sufficient to be engulfed by phagocytotic monocytes. In certain embodiments, the paramagnetic particles are commercially available beads, for example, those produced by Dynal AS under the trade name Dynabeads™ Exemplary Dynabeads™ in this regard are M-280, M-450, and M-500. In one aspect, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be expanded. In certain embodiments the irrelevant beads include beads coated with sheep anti-mouse antibodies, goat anti-mouse antibodies, and human serum albumin. In brief, such depletion of monocytes is performed by preincubating PBMC isolated from whole blood or apheresed peripheral blood with one or more varieties of irrelevant or non-antibody coupled paramagnetic particles at any amount that allows for removal of monocytes (approximately a 20:1 bead:cell ratio) for about 30 minutes to 2 hours at 22 to 37.degree. C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL™ Magnetic Particle Concentrator (DYNAL MPC™)). Assurance of requisite depletion can be monitored by a variety of methodologies known to those of ordinary skill in the art, including flow cytometric analysis of CD14 positive cells, before and after said depletion. T cells for stimulation can also be frozen after the washing step, which does not require the monocyte-removal step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80.degree. C. at a rate of 1.degree. per minute and stored in the vapor phase of a liquid nitrogen storage tank. Other methods of controlled freezing may be used as well as uncontrolled freezing immediately at −20.degree. C. or in liquid nitrogen. The culture of T cells may be performed in the presence of regenerative cells. In some embodiments said regenerative cells are pulsed or primed with an immune stimulatory agent. This is to enhance the ability of the regenerative cells to program T cells, or PBMC. In one ideal embodiment patient PMBC are extracted, incubated with regenerative cells and subsequently administered back to the patient. In other embodiments immune cells from the patient are cultured in the conditioned media of regenerative cells. In some embodiments cells are cultured under hypoxia.

In certain embodiments, cryopreserved cells are thawed and washed as described herein and allowed to rest for one hour at room temperature prior to activation using the methods of the present invention.

In some embodiments, the lymphocytes are taken from a partially or fully HLA-matched, non-cancerous donor. T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and 7,572,631 with the exception that they are cultured together with regenerative cells.

Infusion of the immune cell population of the present invention enhances, potentiates, or increases the tolerogenic capacity of the immune response, as well as evokes regenerative potential. Generally, the immune response can include the humoral immune response, the cell-mediated immune response, or both. For example, antigen presentation through an immunological pathway involving MHC II proteins or direct B-cell stimulation can produce a humoral response; and, antigens presented through a pathway involving MHC I proteins can elicit the cellular arm of the immune system. A humoral response can be determined by a standard immunoassay for antibody levels in a serum sample from the subject receiving the pharmaceutically acceptable composition. A cellular immune response is a response that involves T cells and can be determined in vitro or in vivo. For example, a general cellular immune response can be determined as the T cell proliferative activity in cells (e.g., peripheral blood leukocytes (PBLs)) sampled from the subject at a suitable time following the administering of a pharmaceutically acceptable composition. Following incubation of e.g., PBMCs with a stimulator for an appropriate period, [.sup.3H]thymidine incorporation can be determined. The subset of T cells that is proliferating can be determined using flow cytometry. T cell cytotoxicity (CTh) can also be determined.

The pharmaceutically acceptable composition can be administered in a therapeutically or a prophylactically effective amount, wherein the pharmaceutically acceptable composition comprises the lymphocyte population of T cells are enriched for T cells reactive to neo-antigens in the recipient and depleted of T cells reactive to antigens on non-cancerous tissues of the recipient, either alone or in combination with one or more other antigens. Administering the pharmaceutically acceptable composition of the present invention to the subject can be carried out using known procedures, and at dosages and for periods of time sufficient to achieve a desired effect. For example, a therapeutically or prophylactically effective amount of the pharmaceutically acceptable composition, can vary according to factors such as the age, sex, and weight of the subject. Dosage regima can be adjusted by one of ordinary skill in the art to elicit the desired immune response including immune responses that provide therapeutic or prophylactic effects.

Administering can be properly timed by the care giver (e.g., physician, veterinarian), and can depend on the clinical condition of the subject, the objectives of administering, and/or other therapies also being contemplated or administered. In some embodiments, an initial dose can be administered, and the subject monitored for either an immunological or clinical response, preferably both. Suitable means of immunological monitoring include using patient's peripheral blood lymphocyte (PBL) as responders and neoplastic cells as stimulators. An immunological reaction also can be determined by a delayed inflammatory response at the site of administering. One or more doses subsequent to the initial dose can be given as appropriate, typically on a monthly, semimonthly, or preferably a weekly basis, until the desired effect is achieved. Thereafter, additional booster or maintenance doses can be given as required, particularly when the immunological or clinical benefit appears to subside.

The lymphocyte compositions of the present invention may be administered either alone, or as a pharmaceutical composition in combination with diluents and/or with other components such as IL-2 or other cytokines or cell populations. Briefly, pharmaceutical lymphocyte compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In some embodiments of the invention, In certain embodiments, the present invention provides a method of enhancing activity of myeloid derived suppressor cells by exposing said cells to patient liyphocytes that have been conditioned with regenerative cells. In one embodiment, myeloid derived suppressor cells are generated by a means comprising of: a) contacting pluripotent stem cell with an effective amount of kit ligand (KL) (stem cell factor), vascular endothelial growth factor (VEGF), FMS-like tyrosine kinase 3 (Flt3L), thrombopoietin (TPO), and macrophage colony-stimulating factor (M-CSF); and b) culturing said iPSC cells under conditions suitable for propagation of said cell, thereby obtaining a preparation of an isolated MDSC. In certain embodiments, the method further comprises cryopreservation of said MDSC. In yet additional embodiments, the iPSC cell is a mammalian cell. In certain embodiments, the iPSC cell is a human cell. In yet additional embodiments, the isolated MDSC expresses at least one of the cell surface markers selected from the group consisting of CD33, CD115, F4/80, Ly-6C, CD11b, Gr-1, VEGF receptor, CD40 and IL-4R. Other means of generating MDSC are disclosed such as a) contacting a hematopoietic stem cell (HSC) with an effective amount of kit ligand (KL) (stem cell factor), vascular endothelial growth factor (VEGF), FMS-like tyrosine kinase 3 (Flt3L), thrombopoietin (TPO), and macrophage colony-stimulating factor (M-CSF); and b) culturing said HSC under conditions suitable for propagation of said cell, thereby obtaining a preparation of an isolated MDSC. In certain embodiments, the method further comprises cryopreservation of said MDSC. In yet additional embodiments, the HSC is a mammalian HSC. In yet additional embodiments, the HSC is a human HSC. In yet additional embodiments, the isolated MDSC expresses at least one of the cell surface markers selected from the group consisting of CD33, CD115, VEGF receptor, F4/80, Ly-6C, CD11b, Gr-1, CD40 and IL-4R. In other embodiments, the isolated MDSC derived from a human ES cell or human HSC expresses at least one of the cell surface markers selected from the group consisting of CD11b, CD33, CD15, and CD16. In yet other embodiments, the isolated MDSC expresses CD11b and CD33. In still other embodiments, the isolated MDSC expresses CD11b and Gr-1. In yet additional embodiments, the invention provides an isolated MDSC obtained by any of the methods described herein.

The invention, in some embodiments, teaches the application of Immunological tolerance to the condition of alloantigen reactivity and autoimmunity. In one embodiment the invention teaches the treatment of diabetes. In one embodiment the invention teaches the treatment and/or reversion of type 1 diabetes. It is known that a cardinal feature of the immune system, is allowing for recognition and elimination of pathological threats, while selectively ignoring antigens that belong to the body. Traditionally, autoimmune conditions such as type 1 diabetes or conditions associated with cytokine storm, or allograft rejection are treated with non-specific inhibitors of inflammation such as steroids, as well as immune suppressive agents such as cyclosporine, 5-azathrioprine, and methotrexate. These approaches globally suppress immune functions and have numerous undesirable side effects. Unfortunately, given the substantial decrease in quality of life observed in patients with autoimmunity, the potential of alleviation of autoimmune symptoms outweighs the side effects such as opportunistic infections and increased predisposition to neoplasia.

The invention provides novel stem cell types, methods of manufacture, and therapeutic uses. Provided are means of deriving stem cells possessing regenerative, immune modulatory, anti-inflammatory, and angiogenic/neurogenic activity from umbilical cord tissue such as Wharton's Jelly. In some embodiments manipulation of stem cell "potency" is disclosed through hypoxic manipulation, growth on non-xenogeneic conditions, as well as addition of epigenetic modulators.

The cells of the invention are cultured under hypoxia, in one embodiment, cultured in order to induce and/or augment expression of chemokine receptors. One such receptor is CXCR-4. The population of cells, including population of umbilical cord mesenchymal cells, may be enriched for CXCR-4, such as (or such as about) 50%, 55%, 60%, 65%, 70%, 75%, 80%, 85%, 90%, 95%, 96%, 97%, 98%, 99%, or more of the population expressing CXCR-4, CD31, CD34, or any combination thereof. In addition or alternatively, <1%, <2%, <3%, <4%, <5%, <6%, <7%, <8%, <9%, or <10% of the population of cells may express CD14 and/or CD45. The umbilical cord cells of the invention may further possess markers selected from the group consisting of STRO-1, CD105, CD54, CD56, CD106, HLA-I markers, vimentin, ASMA, collagen-1, fibronectin, LFA-3, ICAM-1, PECAM-1, P-selectin, L-selectin, CD49b/CD29, CD49c/CD29, CD49d/CD29, CD61, CD18, CD29, thrombomodulin, telomerase, CD10, CD13, STRO-2, VCAM-1, CD146, and THY-1, and a combination thereof. In some embodiments said placental cells of the invention are admixed with endothelial cells. Said endothelial cells may express one or more markers selected from the group consisting of: a) extracellular vimentin; b) CD133; c) c-kit; d) VEGF receptor; e) activated protein C receptor; and f) a combination thereof. In some embodiments, the population of endothelial cells comprises endothelial progenitor cells.

The population of cells may be allogeneic, autologous, or xenogenic to an individual, including an individual being administered the population of cells. In some embodiments, the population of cells are matched by mixed lymphocyte reaction matching.

In some embodiments, the population of cells is derived from tissue selected from the group consisting of the placental body, placenta, umbilical cord tissue, peripheral blood, hair follicle, cord blood, Wharton's Jelly, menstrual blood, endometrium, skin, omentum, amniotic fluid, and a combination thereof. In some embodiments, the population of cells, the population of umbilical mesenchymal stem cells, or the population of endothelial cells comprises human umbilical cord derived adherent cells. The human umbilical cord derived adherent cells may express a cytokines selected from the group consisting of) FGF-1; b) FGF-2; c) HGF; d) interleukin-1 receptor antagonist; and e) a combination thereof. In some embodiments, the population of cells, the population of umbilical cord cells express arginase, indoleamine 2,3 deoxygenase, interleukin-10, and/or interleukin 35. In some embodiments, the population of cells, the population of umbilical cord cells, or the population of endothelial cells express hTERT and Oct-4 but does not express a STRO-1 marker.

In some embodiments, the population of cells, the population of umbilical cord cells has an ability to undergo cell division in less than 36 hours in a growth medium. In some embodiments, the population of cells, the population of umbilical cord cells has an ability to proliferate at a rate of 0.9-1.2 doublings per 36 hours in growth media. In some embodiments, the population of cells, the population of umbilical cord cells has an ability to proliferate at a rate of 0.9, 1.0, 1.1, or 1.2 doublings per 36 hours in growth media. The population of cells, population of umbilical cord cells may produce exosomes capable of inducing more than 50% proliferation when the exosomes are cultured with human umbilical cord endothelial cells. The induction of proliferation may occur when the exosomes are cultured with the human umbilical cord endothelial cells at a concentration of 10, 20, 30, 40, 50, 60, 70, 80, 90, 100, 110, 120, 130, 140, 150, 160, 170, 180, 190, 200, or more exosomes per cell.

In some embodiments, a population of cells, including a population of umbilical cells alone, are administered to an individual, including an individual having and acute or chronic pathology, wherein the population of cells may be administered via any suitable route, including as non-limiting examples, intramuscularly and/or intravenously.

In some embodiments, a population of umbilical cord cells is optionally obtained, the population is then optionally contacted via culturing with a population of progenitor for T regulatory cells, wherein the culturing conditions allow for the generation of T regulatory cells, then the generated T regulatory cells are administered to an individual.

In another embodiment of the invention, biologically useful immune cells are generated after culture with regenerative cells, and/or stem cells are disclosed, of the mesenchymal or related lineages, which are therapeutically reprogrammed cells having minimal oxidative damage and telomere lengths that compare favorably with the telomere lengths of undamaged, pre-natal or embryonic stem cells (that is, the therapeutically reprogrammed cells of the present invention possess near prime physiological state genomes). Moreover the therapeutically reprogrammed cells of the present invention are immunologically privileged and therefore suitable for therapeutic applications. Additional methods of the present invention provide for the generation of hybrid stem cells. Furthermore, the present invention includes related methods for maturing stem cells made in accordance with the teachings of the present invention into specific host tissues. For use in the current invention, the practitioner is thought that ontogeny of mammalian development provides a central role for stem cells. Early in embryogenesis, cells from the proximal epiblast destined to become germ cells (primordial germ cells) migrate along the genital ridge. These cells express high levels of alkaline phosphatase as well as expressing the transcription factor Oct4. Upon migration and colonization of the genital ridge, the primordial germ cells undergo differentiation into male or female germ cell precursors (primordial sex cells). For the purpose of this invention disclosure, only male primordial sex cells (PSC) will be discussed, but the qualities and properties of male and female primordial sex cells are equivalent and no limitations are implied. During male primordial sex cell development, the primordial stem cells become closely associated with precursor sertoli cells leading to the beginning of the formation of the seminiferous cords. When the primordial germ cells are enclosed in the seminiferous cords, they differentiate into gonocytes that are mitotically quiescent. These gonocytes divide for a few days followed by arrest at G0/G1 phase of the cell cycle. In mice and rats these gonocytes resume division within a few days after birth to generate spermatogonial stem cells and eventually undergo differentiation and meiosis related to spermatogenesis. It is known that embryonic stem cells are cells derived from the inner cell mass of the pre-implantation blastocyst-stage embryo and have the greatest differentiation potential, being capable of giving rise to cells found in all three germ layers of the embryo proper. From a practical standpoint, embryonic stem cells are an artifact of cell culture since, in their natural epiblast environment, they only exist transiently during embryogenesis. Manipulation of embryonic stem cells in vitro has lead to the generation and differentiation of a wide range of cell types, including cardiomyocytes, hematopoietic cells, endothelial cells, nerves, skeletal muscle, chondrocytes, adipocytes, liver and pancreatic islets. Growing embryonic stem cells in co-culture with mature cells can influence and initiate the differentiation of the embryonic stem cells to a particular lineage. Maturation is a process of coordinated steps either forward or backward in the differentiation pathway and can refer to both differentiation and/or dedifferentiation. In one example of the maturation process, a cell, or group of cells, interacts with its cellular environment during embryogenesis and organogenesis. As maturation progresses, cells begin to form niches and these niches, or microenvironments, house stem cells that direct and regulate organogenesis. At the time of birth, maturation has progressed such that cells and appropriate cellular niches are present for the organism to function and survive post-natally. Developmental processes are highly conserved amongst the different species allowing maturation or differentiation systems from one mammalian species to be extended to other mammalian species in the laboratory. During the lifetime of an organism, the cellular composition of the organs and organs systems are exposed to a wide range of intrinsic and extrinsic factors that induce cellular or genomic damage. Ultraviolet light not only has an effect on normal skin cells but also on the skin stem cell population. Chemotherapeutic drugs used to treat cancer have a devastating effect on hematopoietic stem cells. Reactive oxygen species, which are the byproducts of cellular metabolism, are intrinsic factors that compromises the genomic integrity of the cell. In all organs or organ systems, cells are continuously being replaced from stem cell populations. However, as an organism ages, cellular damage accumulates in these stem cell populations. If the damage is inheritable, such as genomic mutations, then all progeny will be effected and thus compromised. A single stem cell clone can contribute to generations of lineages such as lymphoid and myeloid cells for more than a year and therefore have the potential to spread mutations if the stem cell is damaged. The body responds to a compromised stem cell by inducing apoptosis thereby removing it from the pool and preventing potentially dysfunctional or tumorigenic properties. Apoptosis removes compromised cells from the population, but it also decreases the number of stem cells that are available for the future. Therefore, as an organism ages, the number of stem cells decrease. In addition to the loss of the stem cell pool, there is evidence that aging decreases the efficiency of the homing mechanism of stem cells. Telomeres are the physical ends of chromosomes that contain highly conserved, tandemly repeated DNA sequences. Telomeres are involved in the replication and stability of linear DNA molecules and serve as counting mechanism in cells; with each round of cell division the length of the telomeres shortens and at a pre-determined threshold, a signal is activated to initiate cellular senescence. Stem cells and somatic cells produce telomerase, which inhibits shortening of telomeres, but their telomeres still progressively shorten during aging and cellular stress. In one teaching, or embodiment, of the invention, therapeutically reprogrammed cells, in some embodiments mesenchymal stem cells, are provided. Therapeutic reprogramming refers to a maturation process wherein a stem cell is exposed to stimulatory factors according to the teachings of the present invention to yield enhanced therapeutic activity. In some embodiments, enhancement of therapeutic activity may be increase proliferation, in other embodiments, it may be enhanced chemotaxis. Other therapeutic characteristics include ability to under resistance to apoptosis, ability to overcome senescence, ability to differentiate into a variety of different cell types effectively, and ability to secrete therapeutic growth factors which enhance viability/activity, of endogenous stem cells. In order to induce therapeutic reprogramming of cells, in some cases, as disclosed herein, of wharton's jelly originating cells, the invention teaches the utilization of stimulatory factors, including without limitation, chemicals, biochemicals and cellular extracts to change the epigenetic programming of cells. These stimulatory factors induce, among other results, genomic methylation changes in the donor DNA. Embodiments of the present invention include methods for preparing cellular extracts from whole cells, cytoplasts, and karyplasts, although other types of cellular extracts are contemplated as being within the scope of the present invention. In a non-limiting example, the cellular extracts of the present invention are prepared from stem cells, specifically embryonic stem cells. Donor cells are incubated with the chemicals, biochemicals or cellular extracts for defined periods of time, in a non-limiting example for approximately one hour to approximately two hours, and those reprogrammed cells that express embryonic stem cell markers, such as October 4, after a culture period are then ready for transplantation, cryopreservation or further maturation. In another embodiment of the present invention, hybrid stem cells are provided which can be used for cellular regenerative/reparative therapy. The hybrid stem cells of the present invention are pluripotent and customized for the intended recipient so that they are immunologically compatible with the recipient. Hybrid stem cells are a fusion product between a donor cell, or nucleus thereof, and a host cell. Typically the fusion occurs between a donor nucleus and an enucleated host cell. The donor cell can be any diploid cell, including but not limited to, cells from pre-embryos, embryos, fetuses and post-natal organisms. More specifically, the donor cell can be a primordial sex cell, including but not limited to, oogonium or differentiated or undifferentiated spermatogonium, or an embryonic stem cell. Other non-limiting examples of donor cells are therapeutically reprogrammed cells, embryonic stem cells, fetal stem cells and multipotent adult progenitor cells. Preferably the donor cell has the phenotype of the intended recipient. The host cell can be isolated from tissues including, but not limited to, pre-embryos, embryos, fetuses and post-natal organisms and more specifically can include, but is not limited to, embryonic stem cells, fetal stem cells, multipotent adult progenitor cells and adipose-derived stem cells. In a non-limiting example, cultured cell lines can be used as donor cells. The donor and host cells can be from the same individual or different individuals. In one embodiment of the present invention, lymphocytes are used as donor cells and a two-step method is used to purify the donor cells. After the tissues was disassociated, an adhesion step was performed to remove any possible contaminating adherent cells followed by a density gradient purification step. The majority of lymphocytes are quiescent (in G0 phase) and therefore can have a methylation status than conveys greater plasticity for reprogramming. Multipotent or pluripotent stem cells or cell lines useful as donor cells in embodiments of the present invention are functionally defined as stem cells by their ability to undergo differentiation into a variety of cell types including, but not limited to, adipogenic, neurogenic, osteogenic, chondrogenic and cardiogenic cell.

In some embodiments, host cell enucleation for the generation of hybrid stem cells according to the teachings of the present invention can be conducted using a variety of means. In a non-limiting example, ADSCs were plated onto fibronectin coated tissue culture slides and treated with cells with either cytochalasin D or cytochalasin B. After treatment, the cells can be trypsinized, re-plated and are viable for about 72 hours post enucleation. Host cells and donor nuclei can be fused using one of a number of fusion methods known to those of skill in the art, including but not limited to electrofusion, microinjection, chemical fusion or virus-based fusion, and all methods of cellular fusion are envisioned as being within the scope of the present invention. The hybrid stem cells made according to the teachings of the present invention possess surface antigens and receptors from the enucleated host cell but has a nucleus from a developmentally younger cell. Consequently, the hybrid stem cells of the present invention will be receptive to cytokines, chemokines and other cell signaling agents, yet possess a nucleus free from age-related DNA damage. The therapeutically reprogrammed cells and hybrid stem cells made in accordance with the teachings of the present invention are useful in a wide range of therapeutic applications for cellular regenerative/reparative therapy. For example, and not intended as a limitation, the therapeutically reprogrammed cells and hybrid stem cells of the present invention can be used to replenish stem cells in animals whose natural stem cells have been depleted due to age or ablation therapy such as cancer radiotherapy and chemotherapy. In another non-limiting example, the therapeutically reprogrammed cells and hybrid stem cells of the present invention are useful in organ regeneration and tissue repair. In one embodiment of the present invention, therapeutically reprogrammed cells and hybrid stem cells can be used to reinvigorate damaged muscle tissue including dystrophic muscles and muscles damaged by ischemic events such as myocardial infarcts. In another embodiment of the present invention, the therapeutically reprogrammed cells and hybrid stem cells disclosed herein can be used to ameliorate scarring in animals, including humans, following a traumatic injury or surgery. In this embodiment, the therapeutically reprogrammed cells and hybrid stem cells of the present invention are administered systemically, such as intravenously, and migrate to the site of the freshly traumatized tissue recruited by circulating cytokines secreted by the damaged cells. In another embodiment of the present invention, the therapeutically reprogrammed cells and hybrid stem cells can be administered locally to a treatment site in need or repair or regeneration.

In one embodiment, umbilical cord samples were obtained following the delivery of normal term babies with Institutional Review Board approval. A portion of the umbilical cord was then cut into approximately 3 cm long segments. The segments were then placed immediately into 25 ml of phosphate buffered saline without calcium and magnesium (PBS) and 1.times. antibiotics (100 U/ml penicillin, 100 ug/ml streptomycin, 0.025 ug/ml amphotericin B). The tubes were then brought to the lab for dissection within 6 hours. Each 3 cm umbilical cord segment was dissected longitudinally utilizing aseptic technique. The tissue was carefully undermined and the umbilical vein and both umbilical arteries were removed. The remaining segment was sutured inside out and incubated in 25 ml of PBS, 1.times. antibiotic, and 1 mg/ml of collagenase at room temperature. After 16-18 hours the remaining suture and connective tissue was removed and discarded. The cell suspension was separated equally into two tubes, the cells were washed 3.times. by diluting with PBS to yield a final volume of 50 ml per tube, and then centrifuged. Red blood cells were then lysed using a hypotonic solution. Cells were plated onto 6-well plates at a concentration of 5-20.times.10.sup.6 cells per well. UC-MSC were cultured in low-glucose DMEM (Gibco) with 10% FBS (Hyclone), 2 mM L-Glutamine (Gibco), 100 U/ml penicillin, 100 ug/ml streptomycin, 0.025 ug/ml amphotericin B (Gibco). Cells were washed 48 hours after the initial plating with PBS and given fresh media. Cell culture media were subsequently changed twice a week through half media changes. After 7 days or approximately 70-80% confluence, cells were passed using HyQTase (Hyclone) into a 10 cm plate. Cells were then regularly passed 1:2 every 7 days or upon reaching 80% confluence. Alternatively, 0.25% HQ trypsin/EDTA (Hyclone) was used to passage cells in a similar manner.

In one embodiment, tolerogenic dendritic cells may be pulsed with diabetogenic antigens in order to induce an immune response that is tolerogenic, which is subsequently amplified by myeloid derived suppressor cells, and/or IMMCELZ™. Generation of tolerogenic dendritic cells may be accomplished by manipulating existing protocols for generation of dendritic cells by adding a maturation inhibition step. Protocols used for generating dendritic cells have been described in the literature and are incorporated by reference in melanoma [114-165], soft tissue sarcoma [166], thyroid [167-169], glioma [170-191], multiple myeloma ,[192-200], lymphoma [201-203], leukemia [204-211], as well as liver [212-217], lung [218-231], ovarian [232-235], and pancreatic cancer [236-238].

In some embodiments of the invention, administration of cells of the invention is performed for suppression of an inflammatory and/or autoimmune disease. In these situations, it may be necessary to utilize an immune suppressive/ or therapeutic adjuvant. Immune suppressants are known in the art and can be selected from a group comprising of: cyclosporine, rapamycin, campath-1H, ATG, Prograf, anti IL-2r, MMF, FTY, LEA, cyclosporin A, diftitox, denileukin, levamisole, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, and trimetrexate), purine analogs (e.g., cladribine, fludarabine, 6-mercaptopurine, thiamiprine, and thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, and tegafur) fluocinolone, triaminolone, anecortave acetate, fluorometholone, medrysone, prednislone, etc. In another embodiment, the use of stem cell conditioned media may be used to potentiate an existing anti-inflammatory agent. Anti-inflammatory agents may comprise one or more agents including NSAIDs, interleukin-1 antagonists, dihydroorotate synthase inhibitors, p38 MAP kinase inhibitors, TNF-α inhibitors, TNF-α sequestration agents, and methotrexate. More specifically, anti-inflammatory agents may comprise one or more of, e.g., anti-TNF-α, lysophylline, alpha 1-antitrypsin (AAT), interleukin-10 (IL-10), pentoxyfilline, COX-2 inhibitors, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (eg., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), epsilon.-acetamidocaproic acid, s-adenosylmethionine, 3-amino-4-hydroxybutyric .acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, candelilla wax, alpha bisabolol, aloe vera, Manjistha, Guggal, kola extract, chamomile, sea whip extract, glycyrrhetic acid, glycyrrhizic acid, oil soluble licorice extract, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid.

EXAMPLES

Synergistic protection from Diabetes Induction by IMMCELZ™ and Inducers of Myeloid Suppressor Cells IMMCELZ™ are a proprietary type of treated T regulatory cells that have regenerative properies, that were generated by culture of NOD splenocytes in conditioned media of umbilical cord derived mesenchymal stem cells (MSC) that were pulsed with interferon gamma, 100 IU/million cells. Conditioned media was standardized by HGF-1 concentration with a desired concentration of 200 pg/ml of HGF-1. Cells were cultured for 48 hours in presence of IL-2 40 IU/ml and subsequently frozen.

IMMCELZ™ was administered at a concentration of 500,000 cells intravenously by tail vein on day of BCG administration.

BCG vaccine [50 µl containing around $10^5$ colony-forming units (CFU)] was administered subcutaneously at the base of the tail when NOD mice were 7 weeks old. Results are shown in FIG. 1.

Figure 2:
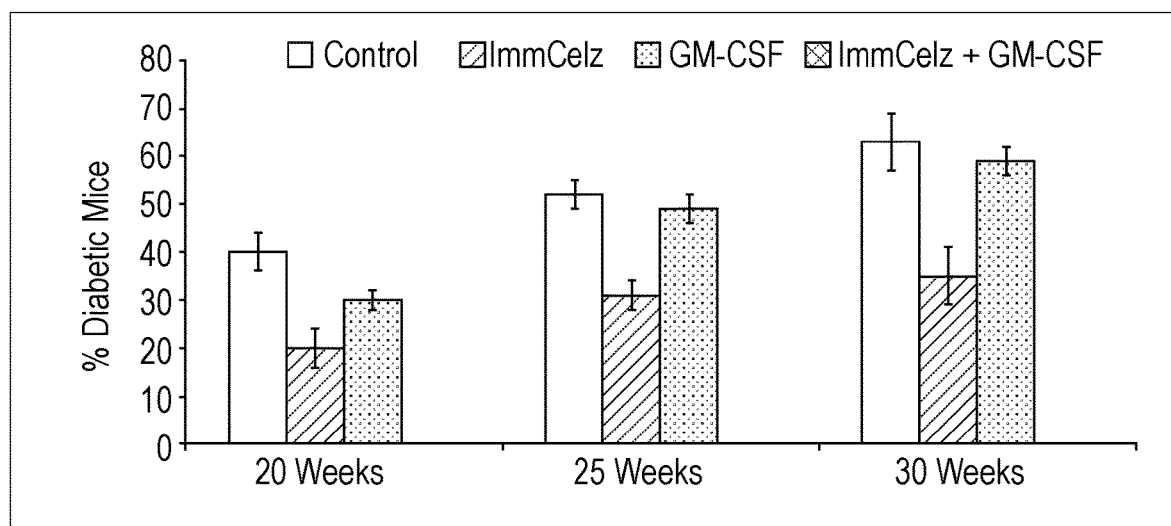
FIG. 2 is a bar graph showing the effects of GM-CSF and IMMCELZ™ on diabetic mice.

GM-CSF was administered at i.p. injection of 100 ng/mouse of recombinant murine GM-CSF (R&D Systems) or PBS. Mice were injected three times per week for the first 3 wk, followed by two injections per week up until completion of experiment. Results are shown in FIG. 2.

REFERENCES

1. Graca, L., B. Silva-Santos, and A. Coutinho, *The blindspot of regulatory T cells*. Eur J Immunol, 2006. 36(4): p. 802-5.
2. Lehner, T., *Special regulatory T cell review: The resurgence of the concept of contrasuppression in immunoregulation*. Immunology, 2008. 123(1): p. 40-4.
3. Cools, N., et al., *Regulatory T cells and human disease*. Clin Dev Immunol, 2007. 2007: p. 89195.
4. Yamazaki, S. and R. M. Steinman, *Dendritic cells as controllers of antigen-specific Foxp3+ regulatory T cells*. J Dermatol Sci, 2009. 54(2): p. 69-75.
5. Curotto de Lafaille, M. A. and J. J. Lafaille, *Natural and adaptive foxp3+ regulatory T cells: more of the same or a division of labor*? Immunity, 2009. 30(5): p. 626-35.
6. Shalev, I., et al., *Making sense of regulatory T cell suppressive function*. Semin Immunol, 2011. 23(4): p. 282-92.
7. Kushwah, R. and J. Hu, *Role of dendritic cells in the induction of regulatory T cells*. Cell Biosci, 2011. 1(1): p. 20.
8. Gravano, D. M. and D. A. Vignali, *The battle against immunopathology: infectious tolerance mediated by regulatory T cells*. Cell Mol Life Sci, 2012. 69(12): p. 1997-2008.
9. Namdev, P., et al., *Monocytic-Myeloid Derived Suppressor Cells of HIV-Infected Individuals With Viral Suppression*

*Exhibit Suppressed Innate Immunity to Mycobacterium tuberculosis.* Front Immunol, 2021. 12: p. 647019.
10. Nagaraj, S., et al., Mechanism of T cell tolerance induced by myeloid-derived suppressor cells. J Immunol, 2010. 184(6): p. 3106-16.
11. Sinha, P., V. K. Clements, and S. Ostrand-Rosenberg, *Reduction of myeloid-derived suppressor cells and induction of M1 macrophages facilitate the rejection of established metastatic disease.* J Immunol, 2005. 174(2): p. 636-45.
12. Bunt, S. K., et al., *Inflammation induces myeloid-derived suppressor cells that facilitate tumor progression.* J Immunol, 2006. 176(1): p. 284-90.
13. Ochoa, A. C., et al., *Arginase, prostaglandins, and myeloid-derived suppressor cells in renal cell carcinoma.* Clin Cancer Res, 2007. 13(2 Pt 2): p. 721s-726s.
14. Sinha, P., et al., *Cross-talk between myeloid-derived suppressor cells and macrophages subverts tumor immunity toward a type 2 response.* J Immunol, 2007. 179(2): p. 977-83.
15. Talmadge, J. E., *Pathways mediating the expansion and immunosuppressive activity of myeloid-derived suppressor cells and their relevance to cancer therapy.* Clin Cancer Res, 2007. 13(18 Pt 1): p. 5243-8.
16. Movahedi, K., et al., *Identification of discrete tumor-induced myeloid-derived suppressor cell subpopulations with distinct T cell-suppressive activity.* Blood, 2008. 111(8): p. 4233-44.
17. Sawanobori, Y., et al., *Chemokine-mediated rapid turnover of myeloid-derived suppressor cells in tumor-bearing mice.* Blood, 2008. 111(12): p. 5457-66.
18. Nagaraj, S. and D. I. Gabrilovich, *Tumor escape mechanism governed by myeloid-derived suppressor cells.* Cancer Res, 2008. 68(8): p. 2561-3.
19. Serafini, P., et al., *Myeloid-derived suppressor cells promote cross-tolerance in B-cell lymphoma by expanding regulatory T cells.* Cancer Res, 2008. 68(13): p. 5439-49.
20. Watanabe, S., et al., *Tumor-induced CD11b+Gr-1+myeloid cells suppress T cell sensitization in tumor-draining lymph nodes.* J Immunol, 2008. 181(5): p. 3291-300.
21. Youn, J. I., et al., *Subsets of myeloid-derived suppressor cells in tumor-bearing mice.* J Immunol, 2008. 181(8): p. 5791-802.
22. Rodriguez, P. C., et al., *Arginase I-producing myeloid-derived suppressor cells in renal cell carcinoma are a subpopulation of activated granulocytes.* Cancer Res, 2009. 69(4): p. 1553-60.
23. Ostrand-Rosenberg, S. and P. Sinha, *Myeloid-derived suppressor cells: linking inflammation and cancer.* J Immunol, 2009. 182(8): p. 4499-506.
24. Stewart, T. J., et al., *Modulating the expression of IFN regulatory factor 8 alters the protumorigenic behavior of CD11b+Gr-1+ myeloid cells.* J Immunol, 2009. 183(1): p. 117-28.
25. Ilkovitch, D. and D. M. Lopez, *The liver is a site for tumor-induced myeloid-derived suppressor cell accumulation and immunosuppression.* Cancer Res, 2009. 69(13): p. 5514-21.
26. Hoechst, B., et al., *Myeloid derived suppressor cells inhibit natural killer cells in patients with hepatocellular carcinoma via the NKp30 receptor.* Hepatology, 2009. 50(3): p. 799-807.
27. Pan, P. Y., et al., *Immune stimulatory receptor CD40 is required for T-cell suppression and T regulatory cell activation mediated by myeloid-derived suppressor cells in cancer.* Cancer Res, 2010. 70(1): p. 99-108.
28. Poschke, I., et al., *Immature immunosuppressive CD14+ HLA-DR-/low cells in melanoma patients are Stat3hi and overexpress CD80, CD83, and DC-sign.* Cancer Res, 2010. 70(11): p. 4335-45.
29. Dugast, A. S., et al., *Myeloid-derived suppressor cells accumulate in kidney allograft tolerance and specifically suppress effector T cell expansion.* J Immunol, 2008. 180(12): p. 7898-906.
30. Zhang, W., et al., *Human inhibitory receptor immunoglobulin-like transcript 2 amplifies CD11b+Gr1+ myeloid-derived suppressor cells that promote long-term survival of allografts.* Transplantation, 2008. 86(8): p. 1125-34.
31. Dugast, A. S. and B. Vanhove, *Immune regulation by non-lymphoid cells in transplantation.* Clin Exp Immunol, 2009. 156(1): p. 25-34.
32. De Wilde, V., et al., *Endotoxin-induced myeloid-derived suppressor cells inhibit alloimmune responses via heme oxygenase-1.* Am J Transplant, 2009. 9(9): p. 2034-47.
33. Natarajan, S. and A. W. Thomson, *Tolerogenic dendritic cells and myeloid-derived suppressor cells: potential for regulation and therapy of liver auto- and alloimmunity.* Immunobiology, 2010. 215(9-10): p. 698-703.
34. Boros, P., et al., *Myeloid-derived suppressor cells: natural regulators for transplant tolerance.* Hum Immunol, 2010. 71(11): p. 1061-6.
35. Adeegbe, D., et al., *In vivo induction of myeloid suppressor cells and CD4(+)Foxp3(+) T regulatory cells prolongs skin allograft survival in mice.* Cell Transplant, 2011. 20(6): p. 941-54.
36. Highfill, S. L., et al., *Bone marrow myeloid-derived suppressor cells (MDSCs) inhibit graft-versus-host disease (GVHD) via an arginase-1-dependent mechanism that is up-regulated by interleukin-13.* Blood, 2010. 116(25): p. 5738-47.
37. Serafini, P., et al., *Phosphodiesterase-5 inhibition augments endogenous antitumor immunity by reducing myeloid-derived suppressor cell function.* J Exp Med, 2006. 203(12): p. 2691-702.
38. Nefedova, Y., et al., *Mechanism of all-trans retinoic acid effect on tumor-associated myeloid-derived suppressor cells.* Cancer Res, 2007. 67(22): p. 11021-8.
39. Melani, C., et al., *Amino-biphosphonate-mediated MMP-9 inhibition breaks the tumor-bone marrow axis responsible for myeloid-derived suppressor cell expansion and macrophage infiltration in tumor stroma.* Cancer Res, 2007. 67(23): p. 11438-46.
40. Ko, J. S., et al., *Sunitinib mediates reversal of myeloid-derived suppressor cell accumulation in renal cell carcinoma patients.* Clin Cancer Res, 2009. 15(6): p. 2148-57.
41. Nagaraj, S., et al., *Anti-inflammatory triterpenoid blocks immune suppressive function of MDSCs and improves immune response in cancer.* Clin Cancer Res, 2010. 16(6): p. 1812-23.
42. Vincent, J., et al., *5-Fluorouracil selectively kills tumor-associated myeloid-derived suppressor cells resulting in enhanced T cell-dependent antitumor immunity.* Cancer Res, 2010. 70(8): p. 3052-61.
43. Veltman, J. D., et al., *COX-2 inhibition improves immunotherapy and is associated with decreased numbers of myeloid-derived suppressor cells in mesothelioma. Celecoxib influences MDSC function.* BMC Cancer, 2010. 10: p. 464.
44. Li, H., et al., *Cancer-expanded myeloid-derived suppressor cells induce anergy of NK cells through membrane-bound TGF-beta 1.* J Immunol, 2009. 182(1): p. 240-9.

45. Mandruzzato, S., et al., *IL4Ralpha+myeloid-derived suppressor cell expansion in cancer patients.* J Immunol, 2009. 182(10): p. 6562-8.
46. Zheng, Z., et al., *IL-6 Promotes the Proliferation and Immunosuppressive Function of Myeloid-Derived Suppressor Cells via the MAPK Signaling Pathway in Bladder Cancer.* Biomed Res Int, 2021. 2021: p. 5535578.
47. Smith, A. D., et al., *Autocrine IL6-Mediated Activation of the STAT3-DNMT Axis Silences the TNFalpha-RIP1 Necroptosis Pathway to Sustain Survival and Accumulation of Myeloid-Derived Suppressor Cells.* Cancer Res, 2020. 80(15): p. 3145-3156.
48. Ibrahim, M. L., et al., *Expression profiles and function of IL6 in polymorphonuclear myeloid-derived suppressor cells.* Cancer Immunol Immunother, 2020. 69(11): p. 2233-2245.
49. Xu, Z., et al., *Upregulation of IL-6 in CUL4B-deficient myeloid-derived suppressive cells increases the aggressiveness of cancer cells.* Oncogene, 2019. 38(30): p. 5860-5872.
50. Tomic, S., et al., *Prostaglanin-E2 Potentiates the Suppressive Functions of Human Mononuclear Myeloid-Derived Suppressor Cells and Increases Their Capacity to Expand IL-10-Producing Regulatory T Cell Subsets.* Front Immunol, 2019. 10: p. 475.
51. Cheng, P., et al., *Inhibition of dendritic cell differentiation and accumulation of myeloid-derived suppressor cells in cancer is regulated by S100A9 protein.* J Exp Med, 2008. 205(10): p. 2235-49.
52. Xiang, X., et al., *Induction of myeloid-derived suppressor cells by tumor exosomes.* Int J Cancer, 2009. 124(11): p. 2621-33.
53. Liu, Y., et al., *Contribution of MyD88 to the tumor exosome-mediated induction of myeloid derived suppressor cells.* Am J Pathol, 2010. 176(5): p. 2490-9.
54. Greifenberg, V., et al., *Myeloid-derived suppressor cell activation by combined LPS and IFN-gamma treatment impairs DC development.* Eur J Immunol, 2009. 39(10): p. 2865-76.
55. Morales, J. K., et al., *GM-CSF is one of the main breast tumor-derived soluble factors involved in the differentiation of CD11b-Gr1-bone marrow progenitor cells into myeloid-derived suppressor cells.* Breast Cancer Res Treat, 2010. 123(1): p. 39-49.
56. Dolcetti, L., et al., *Hierarchy of immunosuppressive strength among myeloid-derived suppressor cell subsets is determined by GM-CSF.* Eur J Immunol, 2010. 40(1): p. 22-35.
57. Lee, J. M., et al., *Agonistic Anti-CD137 Monoclonal Antibody Treatment Induces C11bGr-1 Myeloid-derived Suppressor Cells.* Immune Netw, 2010. 10(3): p. 104-8.
58. Priceman, S. J., et al., *Targeting distinct tumor-infiltrating myeloid cells by inhibiting CSF-1 receptor: combating tumor evasion of antiangiogenic therapy.* Blood, 2010. 115(7): p. 1461-71.
59. Martino, A., et al., *Mycobacterium bovis bacillus Calmette-Guerin vaccination mobilizes innate myeloid-derived suppressor cells restraining in vivo T cell priming via IL-1R-dependent nitric oxide production.* J Immunol, 2010. 184(4): p. 2038-47.
60. Zhang, H. and G. G. Meadows, *Chronic alcohol consumption enhances myeloid-derived suppressor cells in B16BL6 melanoma-bearing mice.* Cancer Immunol Immunother, 2010. 59(8): p. 1151-9.
61. Xiang, X., et al., *TLR2-mediated expansion of MDSCs is dependent on the source of tumor exosomes.* Am J Pathol, 2010. 177(4): p. 1606-10.
62. Sander, L. E., et al., *Hepatic acute-phase proteins control innate immune responses during infection by promoting myeloid-derived suppressor cell function.* J Exp Med, 2010. 207(7): p. 1453-64.
63. Dardalhon, V., et al., *Tim-3/galectin-9 pathway: regulation of Th1 immunity through promotion of CD11b+Ly-6G+ myeloid cells.* J Immunol, 2010. 185(3): p. 1383-92.
64. Rodriguez, P. C. and A. C. Ochoa, *Arginine regulation by myeloid derived suppressor cells and tolerance in cancer: mechanisms and therapeutic perspectives.* Immunol Rev, 2008. 222: p. 180-91.
65. Xu, L., et al., *IL-17-producing gammadelta T cells ameliorate intestinal acute graft-versus-host disease by recruitment of Gr-1(+)CD11b(+) myeloid-derived suppressor cells.* Bone Marrow Transplant, 2021.
66. Nicholson, L. B., B. J. Raveney, and M. Munder, *Monocyte dependent regulation of autoimmune inflammation.* Curr Mol Med, 2009. 9(1): p. 23-9.
67. Carmi, Y., et al., *Microenvironment-derived IL-1 and IL-17 interact in the control of lung metastasis.* J Immunol, 2011. 186(6): p. 3462-71.
68. Ma, S., et al., *IL-17A produced by gammadelta T cells promotes tumor growth in hepatocellular carcinoma.* Cancer Res, 2014. 74(7): p. 1969-82.
69. Wu, P., et al., *gammadeltaT17 cells promote the accumulation and expansion of myeloid-derived suppressor cells in human colorectal cancer.* Immunity, 2014. 40(5): p. 785-800.
70. Yang, Z., et al., *Mast cells mobilize myeloid-derived suppressor cells and Treg cells in tumor microenvironment via IL-17 pathway in murine hepatocarcinoma model.* PLoS One, 2010. 5(1): p. e8922.
71. He, D., et al., *IL-17 promotes tumor development through the induction of tumor promoting microenvironments at tumor sites and myeloid-derived suppressor cells.* J Immunol, 2010. 184(5): p. 2281-8.
72. Nausch, N., et al., *Mononuclear myeloid-derived "suppressor" cells express RAE-1 and activate natural killer cells.* Blood, 2008. 112(10): p. 4080-9.
73. Kujawski, M., et al., *Stat3 mediates myeloid cell-dependent tumor angiogenesis in mice.* J Clin Invest, 2008. 118(10): p. 3367-77.
74. Srivastava, M. K., et al., *Myeloid-derived suppressor cells inhibit T-cell activation by depleting cystine and cysteine.* Cancer Res, 2010. 70(1): p. 68-77.
75. Tavira, B., et al., *Effect of simultaneous vaccination with H1N1 and GAD-alum on GAD65-induced immune response.* Diabetologia, 2017. 60(7): p. 1276-1283.
76. Ludvigsson, J., et al., *GAD-treatment of children and adolescents with recent-onset type 1 diabetes preserves residual insulin secretion after 30 months.* Diabetes Metab Res Rev, 2014. 30(5): p. 405-14.
77. Krause, S., et al., *GAD autoantibody affinity in adult patients with latent autoimmune diabetes, the study participants of a GAD65 vaccination trial.* Diabetes Care, 2014. 37(6): p. 1675-80.
78. Ludvigsson, J., et al., *Extended evaluation of the safety and efficacy of GAD treatment of children and adolescents with recent-onset type 1 diabetes: a randomised controlled trial.* Diabetologia, 2011. 54(3): p. 634-40.
79. Ludvigsson, J., *GAD65: a prospective vaccine for treating Type 1 diabetes?* Expert Opin Biol Ther, 2017. 17(8): p. 1033-1043.
80. Axelsson, S., et al., *Cellular and humoral immune responses in type 1 diabetic patients participating in a phase III GAD-alum intervention trial.* Diabetes Care, 2013. 36(11): p. 3418-24.

81. Ludvigsson, J., et al., *GAD treatment and insulin secretion in recent-onset type 1 diabetes.* N Engl J Med, 2008. 359(18): p. 1909-20.

82. Elding Larsson, H., et al., *Safety and efficacy of autoantigen-specific therapy with 2 doses of alum-formulated glutamate decarboxylase in children with multiple islet autoantibodies and risk for type 1 diabetes: A randomized clinical trial.* Pediatr Diabetes, 2018. 19(3): p. 410-419.

83. Ludvigsson, J., et al., *GAD65 antigen therapy in recently diagnosed type 1 diabetes mellitus.* N Engl J Med, 2012. 366(5): p. 433-42.

84. Cheramy, M., et al., *GAD-alum treatment in patients with type 1 diabetes and the subsequent effect on GADA IgG subclass distribution, GAD65 enzyme activity and humoral response.* Clin Immunol, 2010. 137(1): p. 31-40.

85. Lind, A., et al., *A/H1N1 antibodies and TRIB2 autoantibodies in narcolepsy patients diagnosed in conjunction with the Pandemrix vaccination campaign in Sweden 2009-2010.* J Autoimmun, 2014. 50: p. 99-106.

86. Pihl, M., et al., *GAD-specific T cells are induced by GAD-alum treatment in Type-1 diabetes patients.* Clin Immunol, 2017. 176: p. 114-121.

87. Axelsson, S., et al., *Early induction of GAD(65)-reactive Th2 response in type 1 diabetic children treated with alum formulated GAD(65).* Diabetes Metab Res Rev, 2010. 26(7): p. 559-68.

88. Wherrett, D. K., et al., *Antigen-based therapy with glutamic acid decarboxylase (GAD) vaccine in patients with recent-onset type 1 diabetes: a randomised double-blind trial.* Lancet, 2011. 378(9788): p. 319-27.

89. Skoglund, C., et al., *GAD autoantibody epitope pattern after GAD-alum treatment in children and adolescents with type 1 diabetes.* Pediatr Diabetes, 2012. 13(3): p. 244-50.

90. Elding Larsson, H., et al., *Pandemrix(R) vaccination is not associated with increased risk of islet autoimmunity or type 1 diabetes in the TEDDY study children.* Diabetologia, 2018. 61(1): p. 193-202.

91. Agardh, C. D., et al., *GAD65 vaccination: 5 years of follow-up in a randomised dose-escalating study in adult-onset autoimmune diabetes.* Diabetologia, 2009. 52(7): p. 1363-8.

92. Hjorth, M., et al., *GAD-alum treatment induces GAD65-specific CD4+CD25highFOXP3+cells in type 1 diabetic patients.* Clin Immunol, 2011. 138(1): p. 117-26.

93. Axelsson, S., et al., *Long-lasting immune responses 4 years after GAD-alum treatment in children with type 1 diabetes.* PLoS One, 2011. 6(12): p. e29008.

94. Boettler, T., et al., *The clinical and immunological significance of GAD-specific autoantibody and T-cell responses in type 1 diabetes.* J Autoimmun, 2013. 44: p. 40-8.

95. Morales, A. E. and K. M. Thrailkill, *GAD-alum immunotherapy in Type 1 diabetes mellitus.* Immunotherapy, 2011. 3(3): p. 323-32.

96. Bekris, L. M., et al., *GAD65 autoantibody epitopes in adult patients with latent autoimmune diabetes following GAD65 vaccination.* Diabet Med, 2007. 24(5): p. 521-6.

97. Yeo, L. and M. Peakman, *Antigen-specific immunotherapy and influenza vaccination in type 1 diabetes: timing is everything.* Diabetologia, 2017. 60(7): p. 1180-1184.

98. Choat, H. M., et al., *Effect of gamma aminobutyric acid (GABA) or GABA with glutamic acid decarboxylase (GAD) on the progression of type 1 diabetes mellitus in children: Trial design and methodology.* Contemp Clin Trials, 2019. 82: p. 93-100.

99. Ludvigsson, J., *Therapy with GAD in diabetes.* Diabetes Metab Res Rev, 2009. 25(4): p. 307-15.

100. Larsson, H. E. and A. Lernmark, *Does immune-tolerance treatment with Alum-formulated GAD65 protect insulin-production in the pancreatic islet beta cells?* Hum Vaccin, 2011. 7(1): p. 45-9.

101. Arif, S., et al., *GAD-alum immunotherapy in type 1 diabetes expands bifunctional Th1/Th2 autoreactive CD4 T cells.* Diabetologia, 2020. 63(6): p. 1186-1198.

102. Ludvigsson, J., *GAD-alum (Diamyd)—a new concept for preservation of residual insulin secretion.* Expert Opin Biol Ther, 2010. 10(5): p. 787-99.

103. Hannelius, U., C. A. Beam, and J. Ludvigsson, *Efficacy of GAD-alum immunotherapy associated with HLA-DR3-DQ2 in recently diagnosed type 1 diabetes.* Diabetologia, 2020. 63(10): p. 2177-2181.

104. Faustman, D. L., et al., *Proof-of-concept, randomized, controlled clinical trial of Bacillus-Calmette-Guerin for treatment of long-term type 1 diabetes.* PLoS One, 2012. 7(8): p. e41756.

105. Ludvigsson, J., *Autoantigen Treatment in Type 1 Diabetes: Unsolved Questions on How to Select Autoantigen and Administration Route.* Int J Mol Sci, 2020. 21(5).

106. Tavira, B., et al., *Intralymphatic Glutamic Acid Decarboxylase-Alum Administration Induced Th2-Like-Specific Immunomodulation in Responder Patients: A Pilot Clinical Trial in Type 1 Diabetes.* J Diabetes Res, 2018. 2018: p. 9391845.

107. Casas, R., et al., *Glutamic Acid Decarboxylase Injection Into Lymph Nodes: Beta Cell Function and Immune Responses in Recent Onset Type 1 Diabetes Patients.* Front Immunol, 2020. 11: p. 564921.

108. Ludvigsson, J., et al., *Intralymphatic Glutamic Acid Decarboxylase With Vitamin D Supplementation in Recent-Onset Type 1 Diabetes: A Double-Blind, Randomized, Placebo-Controlled Phase IIb Trial.* Diabetes Care, 2021.

109. Ludvigsson, J., et al., *Combined Etanercept, GAD-alum and vitamin D treatment: an open pilot trial to preserve beta cell function in recent onset type 1 diabetes.* Diabetes Metab Res Rev, 2021: p. e3440.

110. Pihl, M., et al., *Regulatory T cell phenotype and function 4 years after GAD-alum treatment in children with type 1 diabetes.* Clin Exp Immunol, 2013. 172(3): p. 394-402.

111. Sinha, P., et al., *Prostaglandin E2 promotes tumor progression by inducing myeloid-derived suppressor cells.* Cancer Res, 2007. 67(9): p. 4507-13.

112. Fricke, I., et al., *Vascular endothelial growth factor-trap overcomes defects in dendritic cell differentiation but does not improve antigen-specific immune responses.* Clin Cancer Res, 2007. 13(16): p. 4840-8.

113. Talmadge, J. E., et al., *Myelostimulatory activity of recombinant human interleukin-2 in mice.* Blood, 1989. 73(6): p. 1458-67.

114. Nestle, F. O., et al., *Vaccination of melanoma patients with peptide-or tumor lysate-pulsed dendritic cells.* Nat Med, 1998. 4(3): p. 328-32.

115. Chakraborty, N. G., et al., *Immunization with a tumor-cell-lysate-loaded autologous-antigen-presenting-cell-based vaccine in melanoma.* Cancer Immunol Immunother, 1998. 47(1): p. 58-64.

116. Wang, F., et al., *Phase I trial of a MART-1 peptide vaccine with incomplete Freund's adjuvant for resected high-risk melanoma.* Clin Cancer Res, 1999. 5(10): p. 2756-65.

117. Thurner, B., et al., *Vaccination with mage-3A1 peptide pulsed mature, monocyte-derived dendritic cells expands* specific cytotoxic T cells and induces regression of some metastases in advanced stage IV melanoma. J Exp Med, 1999. 190(11): p. 1669-78.

118. Thomas, R., et al., *Immature human monocyte-derived dendritic cells migrate rapidly to draining lymph nodes after intradermal injection for melanoma immunotherapy*. Melanoma Res, 1999. 9(5): p. 474-81.

119. Mackensen, A., et al., *Phase I study in melanoma patients of a vaccine with peptide-pulsed dendritic cells generated in vitro from CD34(+) hematopoietic progenitor cells*. Int J Cancer, 2000. 86(3): p. 385-92.

120. Panelli, M. C., et al., *Phase 1 study in patients with metastatic melanoma of immunization with dendritic cells presenting epitopes derived from the melanoma-associated antigens MART-1 and gp100*. J Immunother, 2000. 23(4): p. 487-98.

121. Schuler-Thurner, B., et al., *Mage-3 and influenza-matrix peptide-specific cytotoxic T cells are inducible in terminal stage HLA-A2.1+ melanoma patients by mature monocyte-derived dendritic cells*. J Immunol, 2000. 165(6): p. 3492-6.

122. Lau, R., et al., *Phase I trial of intravenous peptide-pulsed dendritic cells in patients with metastatic melanoma*. J Immunother, 2001. 24(1): p. 66-78.

123. Banchereau, J., et al., *Immune and clinical responses in patients with metastatic melanoma to CD34(+) progenitor-derived dendritic cell vaccine*. Cancer Res, 2001. 61(17): p. 6451-8.

124. Schuler-Thurner, B., et al., *Rapid induction of tumor-specific type 1 T helper cells in metastatic melanoma patients by vaccination with mature, cryopreserved, peptide-loaded monocyte-derived dendritic cells*. J Exp Med, 2002. 195(10): p. 1279-88.

125. Palucka, A. K., et al., *Single injection of CD34+ progenitor-derived dendritic cell vaccine can lead to induction of T-cell immunity in patients with stage IV melanoma*. J Immunother, 2003. 26(5): p. 432-9.

126. Bedrosian, I., et al., *Intranodal administration of peptide pulsed mature dendritic cell vaccines results in superior CD8+ T-cell function in melanoma patients*. J Clin Oncol, 2003. 21(20): p. 3826-35.

127. Slingluff, C. L., Jr., et al., *Clinical and immunologic results of a randomized phase II trial of vaccination using four melanoma peptides either administered in granulocyte-macrophage colony-stimulating factor in adjuvant or pulsed on dendritic cells*. J Clin Oncol, 2003. 21(21): p. 4016-26.

128. Hersey, P., et al., *Phase I/II study of treatment with dendritic cell vaccines in patients with disseminated melanoma*. Cancer Immunol Immunother, 2004. 53(2): p. 125-34.

129. Vilella, R., et al., *Pilot study of treatment of biochemotherapy-refractory stage IV melanoma patients with autologous dendritic cells pulsed with a heterologous melanoma cell line lysate*. Cancer Immunol Immunother, 2004. 53(7): p. 651-8.

130. Palucka, A. K., et al., *Spontaneous proliferation and type 2 cytokine secretion by CD4+T cells in patients with metastatic melanoma vaccinated with antigen-pulsed dendritic cells*. J Clin Immunol, 2005. 25(3): p. 288-95.

131. Banchereau, J., et al., *Immune and clinical outcomes in patients with stage IV melanoma vaccinated with peptide-pulsed dendritic cells derived from CD34+ progenitors and activated with type I interferon*. J Immunother, 2005. 28(5): p. 505-16.

132. Trakatelli, M., et al., *A new dendritic cell vaccine generated with interleukin-3 and interferon-beta induces CD8+ T cell responses against NA17-A2 tumor peptide in elanoma patients*. Cancer Immunol Immunother, 2006. 55(4): p. 469-74.

133. Salcedo, M., et al., *Vaccination of melanoma patients using dendritic cells loaded with an allogeneic tumor cell lysate*. Cancer Immunol Immunother, 2006. 55(7): p. 819-29.

134. Linette, G. P., et al., *Immunization using autologous dendritic cells pulsed with the melanoma-associated antigen gp100-derived G280-9V peptide elicits CD8+immunity*. Clin Cancer Res, 2005. 11(21): p. 7692-9.

135. Escobar, A., et al., *Dendritic cell immunizations alone or combined with low doses of interleukin-2 induce specific immune responses in melanoma patients*. Clin Exp Immunol, 2005. 142(3): p. 555-68.

136. Tuettenberg, A., et al., *Induction of strong and persistent MelanA/MART-1-specific immune responses by adjuvant dendritic cell-based vaccination of stage II melanoma patients*. Int J Cancer, 2006. 118(10): p. 2617-27.

137. Schadendorf, D., et al., *Dacarbazine (DTIC) versus vaccination with autologous peptide-pulsed dendritic cells (DC) in first-line treatment of patients with metastatic melanoma: a randomized phase III trial of the DC study group of the DeCOG*. Ann Oncol, 2006. 17(4): p. 563-70.

138. Di Pucchio, T., et al., *Immunization of stage IV melanoma patients with Melan-A/MART-1 and gp100 peptides plus IFN-alpha results in the activation of specific CD8(+) T cells and monocyte/dendritic cell precursors*. Cancer Res, 2006. 66(9): p. 4943-51.

139. Nakai, N., et al., *Vaccination of Japanese patients with advanced melanoma with peptide, tumor lysate or both peptide and tumor lysate pulsed mature, monocyte-derived dendritic cells*. J Dermatol, 2006. 33(7): p. 462-72.

140. Palucka, A. K., et al., *Dendritic cells loaded with killed allogeneic melanoma cells can induce objective clinical responses and MART-1 specific CD8+ T-cell immunity*. J Immunother, 2006. 29(5): p. 545-57.

141. Lesimple, T., et al., *Immunologic and clinical effects of injecting mature peptide-loaded dendritic cells by intralymphatic and intranodal routes in metastatic melanoma patients*. Clin Cancer Res, 2006. 12(24): p. 7380-8.

142. Guo, J., et al., *Intratumoral injection of dendritic cells in combination with local hyperthermia induces systemic antitumor effect in patients with advanced melanoma*. Int J Cancer, 2007. 120(11): p. 2418-25.

143. O'Rourke, M. G., et al., *Dendritic cell immunotherapy for stage IV melanoma*. Melanoma Res, 2007. 17(5): p. 316-22.

144. Bercovici, N., et al., *Analysis and characterization of antitumor T-cell response after administration of dendritic cells loaded with allogeneic tumor lysate to metastatic melanoma patients*. J Immunother, 2008. 31(1): p. 101-12.

145. Hersey, P., et al., *Phase I/II study of treatment with matured dendritic cells with or without low dose IL-2 in patients with disseminated melanoma*. Cancer Immunol Immunother, 2008. 57(7): p. 1039-51.

146. von Euw, E. M., et al., *A phase I clinical study of vaccination of melanoma patients with dendritic cells loaded with allogeneic apoptotic/necrotic melanoma cells. Analysis of toxicity and immune response to the vaccine and of IL-10-1082 promoter genotype as predictor of disease progression*. J Transl Med, 2008. 6: p. 6.

147. Carrasco, J., et al., *Vaccination of a melanoma patient with mature dendritic cells pulsed with MAGE-3 peptides triggers the activity of nonvaccine anti-tumor cells*. J Immunol, 2008. 180(5): p. 3585-93.

148. Redman, B. G., et al., *Phase Ib trial assessing autologous, tumor-pulsed dendritic cells as a vaccine administered with or without IL-2 in patients with metastatic melanoma.* J Immunother, 2008. 31(6): p. 591-8.

149. Daud, A. I., et al., *Phenotypic and functional analysis of dendritic cells and clinical outcome in patients with high-risk melanoma treated with adjuvant granulocyte macrophage colony-stimulating factor.* J Clin Oncol, 2008. 26(19): p. 3235-41.

150. Engell-Noerregaard, L., et al., *Review of clinical studies on dendritic cell-based vaccination of patients with malignant melanoma: assessment of correlation between clinical response and vaccine parameters.* Cancer Immunol Immunother, 2009. 58(1): p. 1-14.

151. Nakai, N., et al., *Immunohistological analysis of peptide-induced delayed-type hypersensitivity in advanced melanoma patients treated with melanoma antigen pulsed mature monocyte-derived dendritic cell vaccination.* J Dermatol Sci, 2009. 53(1): p. 40-7.

152. Dillman, R. O., et al., *Phase II trial of dendritic cells loaded with antigens from self-renewing, proliferating autologous tumor cells as patient-specific antitumor vaccines in patients with metastatic melanoma: final report.* Cancer Biother Radiopharm, 2009. 24(3): p. 311-9.

153. Chang, J. W., et al., *Immunotherapy with dendritic cells pulsed by autologous dactinomycin-induced melanoma apoptotic bodies for patients with malignant melanoma.* Melanoma Res, 2009. 19(5): p. 309-15.

154. Trepiakas, R., et al., *Vaccination with autologous dendritic cells pulsed with multiple tumor antigens for treatment of patients with malignant melanoma: results from a phase I/II trial.* Cytotherapy, 2010. 12(6): p. 721-34.

155. Jacobs, J. F., et al., *Dendritic cell vaccination in combination with anti-CD25 monoclonal antibody treatment: a phase I/II study in metastatic melanoma patients.* Clin Cancer Res, 2010. 16(20): p. 5067-78.

156. Ribas, A., et al., *Multicenter phase II study of matured dendritic cells pulsed with melanoma cell line lysates in patients with advanced melanoma.* J Transl Med, 2010. 8: p. 89.

157. Ridolfi, L., et al., *Unexpected high response rate to traditional therapy after dendritic cell-based vaccine in advanced melanoma: update of clinical outcome and subgroup analysis.* Clin Dev Immunol, 2010. 2010: p. 504979.

158. Cornforth, A. N., et al., *Resistance to the proapoptotic effects of interferon-gamma on melanoma cells used in patient-specific dendritic cell immunotherapy is associated with improved overall survival.* Cancer Immunol Immunother, 2011. 60(1): p. 123-31.

159. Lesterhuis, W. J., et al., *Wild-type and modified gp100 peptide-pulsed dendritic cell vaccination of advanced melanoma patients can lead to long-term clinical responses independent of the peptide used.* Cancer Immunol Immunother, 2011. 60(2): p. 249-60.

160. Bjoern, J., et al., *Changes in peripheral blood level of regulatory T cells in patients with malignant melanoma during treatment with dendritic cell vaccination and low-dose IL-2.* Scand J Immunol, 2011. 73(3): p. 222-33.

161. Steele, J. C., et al., *Phase I/II trial of a dendritic cell vaccine transfected with DNA encoding melan A and gp100 for patients with metastatic melanoma.* Gene Ther, 2011. 18(6): p. 584-93.

162. Kim, D. S., et al., *Immunotherapy of malignant melanoma with tumor lysate pulsed autologous monocyte-derived dendritic cells.* Yonsei Med J, 2011. 52(6): p. 990-8.

163. Ellebaek, E., et al., *Metastatic melanoma patients treated with dendritic cell vaccination, Interleukin-2 and metronomic cyclophosphamide: results from a phase II trial.* Cancer Immunol Immunother, 2012. 61(10): p. 1791-804.

164. Dillman, R. O., et al., *Tumor stem cell antigens as consolidative active specific immunotherapy: a randomized phase II trial of dendritic cells versus tumor cells in patients with metastatic melanoma.* J Immunother, 2012. 35(8): p. 641-9.

165. Dannull, J., et al., *Melanoma immunotherapy using mature DCs expressing the constitutive proteasome.* J Clin Invest, 2013. 123(7): p. 3135-45.

166. Finkelstein, S. E., et al., *Combination of external beam radiotherapy (EBRT) with intratumoral injection of dendritic cells as neo-adjuvant treatment of high-risk soft tissue sarcoma patients.* Int J Radiat Oncol Biol Phys, 2012. 82(2): p. 924-32.

167. Stift, A., et al., *Dendritic cell vaccination in medullary thyroid carcinoma.* Clin Cancer Res, 2004. 10(9): p. 2944-53.

168. Kuwabara, K., et al., *Results of a phase I clinical study using dendritic cell vaccinations for thyroid cancer.* Thyroid, 2007. 17(1): p. 53-8.

169. Bachleitner-Hofmann, T., et al., *Pilot trial of autologous dendritic cells loaded with tumor lysate(s) from allogeneic tumor cell lines in patients with metastatic medullary thyroid carcinoma.* Oncol Rep, 2009. 21(6): p. 1585-92.

170. Yu, J. S., et al., *Vaccination of malignant glioma patients with peptide-pulsed dendritic cells elicits systemic cytotoxicity and intracranial T-cell infiltration.* Cancer Res, 2001. 61(3): p. 842-7.

171. Yamanaka, R., et al., *Vaccination of recurrent glioma patients with tumour lysate pulsed dendritic cells elicits immune responses: results of a clinical phase I/II trial.* Br J Cancer, 2003. 89(7): p. 1172-9.

172. Yu, J. S., et al., *Vaccination with tumor lysate-pulsed dendritic cells elicits antigen-specific, cytotoxic T-cells in patients with malignant glioma.* Cancer Res, 2004. 64(14): p. 4973-9.

173. Yamanaka, R., et al., *Tumor lysate and IL-18 loaded dendritic cells elicits Th1 response, tumor-specific CD8+ cytotoxic T cells in patients with malignant glioma.* J Neurooncol, 2005. 72(2): p. 107-13.

174. Yamanaka, R., et al., *Clinical evaluation of dendritic cell vaccination for patients with recurrent glioma: results of a clinical phase I/II trial.* Clin Cancer Res, 2005. 11(11): p. 4160-7.

175. Liau, L. M., et al., *Dendritic cell vaccination in glioblastoma patients induces systemic and intracranial T-cell responses modulated by the local central nervous system tumor microenvironment.* Clin Cancer Res, 2005. 11(15): p. 5515-25.

176. Walker, D. G., et al., *Results of a phase I dendritic cell vaccine trial for malignant astrocytoma: potential interaction with adjuvant chemotherapy.* J Clin Neurosci, 2008. 15(2): p. 114-21.

177. Leplina, O. Y., et al., *Use of interferon-alpha-induced dendritic cells in the therapy of patients with malignant brain gliomas.* Bull Exp Biol Med, 2007. 143(4): p. 528-34.

178. De Vleeschouwer, S., et al., *Postoperative adjuvant dendritic cell-based immunotherapy in patients with relapsed glioblastoma multiforme.* Clin Cancer Res, 2008. 14(10): p. 3098-104.

179. Ardon, H., et al., *Adjuvant dendritic cell-based tumour vaccination for children with malignant brain tumours.* Pediatr Blood Cancer, 2010. 54(4): p. 519-25.

180. Prins, R. M., et al., *Gene expression profile correlates with T-cell infiltration and relative survival in glioblastoma*

181. Okada, H., et al., *Induction of CD8+ T-cell responses against novel glioma-associated antigen peptides and clinical activity by vaccinations with {alpha}-type 1 polarized dendritic cells and polyinosinic-polycytidylic acid stabilized by lysine and carboxymethylcellulose in patients with recurrent malignant glioma.* J Clin Oncol, 2011. 29(3): p. 330-6.

182. Fadul, C. E., et al., *Immune response in patients with newly diagnosed glioblastoma multiforme treated with intranodal autologous tumor lysate-dendritic cell vaccination after radiation chemotherapy.* J Immunother, 2011. 34(4): p. 382-9.

183. Chang, C. N., et al., *A phase I/II clinical trial investigating the adverse and therapeutic effects of a postoperative autologous dendritic cell tumor vaccine in patients with malignant glioma.* J Clin Neurosci, 2011. 18(8): p. 1048-54.

184. Cho, D. Y., et al., *Adjuvant immunotherapy with whole-cell lysate dendritic cells vaccine for glioblastoma multiforme: a phase II clinical trial.* World Neurosurg, 2012. 77(5-6): p. 736-44.

185. Iwami, K., et al., *Peptide-pulsed dendritic cell vaccination targeting interleukin-13 receptor alpha2 chain in recurrent malignant glioma patients with HLA-A\*24/A\*02 allele.* Cytotherapy, 2012. 14(6): p. 733-42.

186. Fong, B., et al., *Monitoring of regulatory T cell frequencies and expression of CTLA-4 on T cells, before and after DC vaccination, can predict survival in GBM patients.* PLoS One, 2012. 7(4): p. e32614.

187. De Vleeschouwer, S., et al., *Stratification according to HGG-IMMUNO RPA model predicts outcome in a large group of patients with relapsed malignant glioma treated by adjuvant postoperative dendritic cell vaccination.* Cancer Immunol Immunother, 2012. 61(11): p. 2105-12.

188. Phuphanich, S., et al., *Phase I trial of a multi-epitope-pulsed dendritic cell vaccine for patients with newly diagnosed glioblastoma.* Cancer Immunol Immunother, 2013. 62(1): p. 125-35.

189. Akiyama, Y., et al., *alpha-type-1 polarized dendritic cell-based vaccination in recurrent high-grade glioma: a phase I clinical trial.* BMC Cancer, 2012. 12: p. 623.

190. Prins, R. M., et al., *Comparison of glioma-associated antigen peptide-loaded versus autologous tumor lysate-loaded dendritic cell vaccination in malignant glioma patients.* J Immunother, 2013. 36(2): p. 152-7.

191. Shah, A. H., et al., *Dendritic cell vaccine for recurrent high-grade gliomas in pediatric and adult subjects: clinical trial protocol.* Neurosurgery, 2013. 73(5): p. 863-7.

192. Reichardt, V. L., et al., *Idiotype vaccination using dendritic cells after autologous peripheral blood stem cell transplantation for multiple myeloma—a feasibility study.* Blood, 1999. 93(7): p. 2411-9.

193. Lim, S. H. and R. Bailey-Wood, *Idiotypic protein-pulsed dendritic cell vaccination in multiple myeloma.* Int J Cancer, 1999. 83(2): p. 215-22.

194. Motta, M. R., et al., *Generation of dendritic cells from CD14+ monocytes positively selected by immunomagnetic adsorption for multiple myeloma patients enrolled in a clinical trial of anti-idiotype vaccination.* Br J Haematol, 2003. 121(2): p. 240-50.

195. Reichardt, V. L., et al., *Idiotype vaccination of multiple myeloma patients using monocyte-derived dendritic cells.* Haematologica, 2003. 88(10): p. 1139-49.

196. Guardino, A. E., et al., *Production of myeloid dendritic cells (DC) pulsed with tumor-specific idiotype protein for vaccination of patients with multiple myeloma.* Cytotherapy, 2006. 8(3): p. 277-89.

197. Lacy, M. Q., et al., *Idiotype-pulsed antigen presenting cells following autologous transplantation for multiple myeloma may be associated with prolonged survival.* Am J Hematol, 2009. 84(12): p. 799-802.

198. Yi, Q., et al., *Optimizing dendritic cell-based immunotherapy in multiple myeloma: intranodal injections of idiotype pulsed CD40 ligand-matured vaccines led to induction of type-1 and cytotoxic T-cell immune responses in patients.* Br J Haematol, 2010. 150(5): p. 554-64.

199. Rollig, C., et al., *Induction of cellular immune responses in patients with stage-I multiple myeloma after vaccination with autologous idiotype-pulsed dendritic cells.* J Immunother, 2011. 34(1): p. 100-6.

200. Zahradova, L., et al., *Efficacy and safety of Id-protein-loaded dendritic cell vaccine in patients with multiple myeloma—phase II study results.* Neoplasma, 2012. 59(4): p. 440-9.

201. Timmerman, J. M., et al., *Idiotype pulsed dendritic cell vaccination for B-cell lymphoma: clinical and immune responses in 35 patients.* Blood, 2002. 99(5): p. 1517-26.

202. Maier, T., et al., *Vaccination of patients with cutaneous T-cell lymphoma using intranodal injection of autologous tumor-lysate-pulsed dendritic cells.* Blood, 2003. 102(7): p. 2338-44.

203. Di Nicola, M., et al., *Vaccination with autologous tumor-loaded dendritic cells induces clinical and immunologic responses in indolent B-cell lymphoma patients with relapsed and measurable disease: a pilot study.* Blood, 2009. 113(1): p. 18-27.

204. Hus, I., et al., *Allogeneic dendritic cells pulsed with tumor lysates or apoptotic bodies as immunotherapy for patients with early-stage B-cell chronic lymphocytic leukemia.* Leukemia, 2005. 19(9): p. 1621-7.

205. Li, L., et al., *Immunotherapy for patients with acute myeloid leukemia using autologous dendritic cells generated from leukemic blasts.* Int J Oncol, 2006. 28(4): p. 855-61.

206. Roddie, H., et al., *Phase I/II study of vaccination with dendritic-like leukaemia cells for the immunotherapy of acute myeloid leukaemia.* Br J Haematol, 2006. 133(2): p. 152-7.

207. Litzow, M. R., et al., *Testing the safety of clinical-grade mature autologous myeloid DC in a phase I clinical immunotherapy trial of CML.* Cytotherapy, 2006. 8(3): p. 290-8.

208. Westermann, J., et al., *Vaccination with autologous non-irradiated dendritic cells in patients with bcr/abl+ chronic myeloid leukaemia.* Br J Haematol, 2007. 137(4): p. 297-306.

209. Hus, I., et al., *Vaccination of B-CLL patients with autologous dendritic cells can change the frequency of leukemia antigen-specific CD8+ T cells as well as CD4+CD25+FoxP3+ regulatory T cells toward an antileukemia response.* Leukemia, 2008. 22(5): p. 1007-17.

210. Palma, M., et al., *Development of a dendritic cell-based vaccine for chronic lymphocytic leukemia.* Cancer Immunol Immunother, 2008. 57(11): p. 1705-10.

211. Van Tendeloo, V. F., et al., *Induction of complete and molecular remissions in acute myeloid leukemia by Wilms' tumor 1 antigen-targeted dendritic cell vaccination.* Proc Natl Acad Sci USA, 2010. 107(31): p. 13824-9.

212. Iwashita, Y., et al., *A phase I study of autologous dendritic cell-based immunotherapy for patients with unresectable primary liver cancer.* Cancer Immunol Immunother, 2003. 52(3): p. 155-61.

213. Lee, W. C., et al., *Vaccination of advanced hepatocellular carcinoma patients with tumor lysate pulsed dendritic cells: a clinical trial.* J Immunother, 2005. 28(5): p. 496-504.

214. Butterfield, L. H., et al., *A phase I/II trial testing immunization of hepatocellular carcinoma patients with dendritic cells pulsed with four alpha-fetoprotein peptides.* Clin Cancer Res, 2006. 12(9): p. 2817-25.

215. Palmer, D. H., et al., *A phase II study of adoptive immunotherapy using dendritic cells pulsed with tumor lysate in patients with hepatocellular carcinoma.* Hepatology, 2009. 49(1): p. 124-32.

216. El Ansary, M., et al., *Immunotherapy by autologous dendritic cell vaccine in patients with advanced HCC.* J Cancer Res Clin Oncol, 2013. 139(1): p. 39-48.

217. Tada, F., et al., *Phase I/II study of immunotherapy using tumor antigen-pulsed dendritic cells in patients with hepatocellular carcinoma.* Int J Oncol, 2012. 41(5): p. 1601-9.

218. Ueda, Y., et al., *Dendritic cell-based immunotherapy of cancer with carcinoembryonic antigen-derived, HLA-A24-restricted CTL epitope: Clinical outcomes of 18 patients with metastatic gastrointestinal or lung adenocarcinomas.* Int J Oncol, 2004. 24(4): p. 909-17.

219. Hirschowitz, E. A., et al., *Autologous dendritic cell vaccines for non-small-cell lung cancer.* J Clin Oncol, 2004. 22(14): p. 2808-15.

220. Chang, G. C., et al., *A pilot clinical trial of vaccination with dendritic cells pulsed with autologous tumor cells derived from malignant pleural effusion in patients with late-stage lung carcinoma.* Cancer, 2005. 103(4): p. 763-71.

221. Yannelli, J. R., et al., *The large scale generation of dendritic cells for the immunization of patients with non-small cell lung cancer (NSCLC).* Lung Cancer, 2005. 47(3): p. 337-50.

222. Ishikawa, A., et al., *A phase I study of alpha-galactosylceramide (KRN7000)-pulsed dendritic cells in patients with advanced and recurrent non-small cell lung cancer.* Clin Cancer Res, 2005. 11(5): p. 1910-7.

223. Antonia, S. J., et al., *Combination of p53 cancer vaccine with chemotherapy in patients with extensive stage small cell lung cancer.* Clin Cancer Res, 2006. 12(3 Pt 1): p. 878-87.

224. Perrot, I., et al., *Dendritic cells infiltrating human non-small cell lung cancer are blocked at immature stage.* J Immunol, 2007. 178(5): p. 2763-9.

225. Hirschowitz, E. A., et al., *Immunization of NSCLC patients with antigen-pulsed immature autologous dendritic cells.* Lung Cancer, 2007. 57(3): p. 365-72.

226. Baratelli, F., et al., *Pre-clinical characterization of GMP grade CCL21-gene modified dendritic cells for application in a phase I trial in non-small cell lung cancer.* J Transl Med, 2008. 6: p. 38.

227. Hegmans, J. P., et al., *Consolidative dendritic cell-based immunotherapy elicits cytotoxicity against malignant mesothelioma.* Am J Respir Crit Care Med, 2010. 181(12): p. 1383-90.

228. Um, S. J., et al., *Phase I study of autologous dendritic cell tumor vaccine in patients with non-small cell lung cancer.* Lung Cancer, 2010. 70(2): p. 188-94.

229. Chiappori, A. A., et al., *INGN-225: a dendritic cell-based p53 vaccine (Ad.p53-DC) in small cell lung cancer: observed association between immune response and enhanced chemotherapy effect.* Expert Opin Biol Ther, 2010. 10(6): p. 983-91.

230. Perroud, M. W., Jr., et al., *Mature autologous dendritic cell vaccines in advanced non-small cell lung cancer: a phase I pilot study.* J Exp Clin Cancer Res, 2011. 30: p. 65.

231. Skachkova, O. V., et al., *Immunological markers of anti-tumor dendritic cells vaccine efficiency in patients with non-small cell lung cancer.* Exp Oncol, 2013. 35(2): p. 109-13.

232. Hernando, J. J., et al., *Vaccination with autologous tumour antigen pulsed dendritic cells in advanced gynaecological malignancies: clinical and immunological evaluation of a phase I trial.* Cancer Immunol Immunother, 2002. 51(1): p. 45-52.

233. Rahma, O. E., et al., *A gynecologic oncology group phase II trial of two p53 peptide vaccine approaches: subcutaneous injection and intravenous pulsed dendritic cells in high recurrence risk ovarian cancer patients.* Cancer Immunol Immunother, 2012. 61(3): p. 373-84.

234. Chu, C. S., et al., *Phase I/II randomized trial of dendritic cell vaccination with or without cyclophosphamide for consolidation therapy of advanced ovarian cancer in first or second remission.* Cancer Immunol Immunother, 2012. 61(5): p. 629-41.

235. Kandalaft, L. E., et al., *A Phase I vaccine trial using dendritic cells pulsed with autologous oxidized lysate for recurrent ovarian cancer.* J Transl Med, 2013. 11: p. 149.

236. Lepisto, A. J., et al., *A phase I/II study of a MUC1 peptide pulsed autologous dendritic cell vaccine as adjuvant therapy in patients with resected pancreatic and biliary tumors.* Cancer Ther, 2008. 6(B): p. 955-964.

237. Rong, Y., et al., *A phase I pilot trial of MUC1-peptide-pulsed dendritic cells in the treatment of advanced pancreatic cancer.* Clin Exp Med, 2012. 12(3): p. 173-80.

238. Endo, H., et al., *Phase I trial of preoperative intratumoral injection of immature dendritic cells and OK-432 for resectable pancreatic cancer patients.* J Hepatobiliary Pancreat Sci, 2012. 19(4): p. 465-75.

The invention claimed is:

1. A method of treating type 1 diabetes comprising the steps of: a) selecting a patient suffering from type 1 diabetes; b) extracting an immune cell population comprising T regulatory cells from said patient; c) exposing said immune cell population to interleukin-2 (IL-2) and conditioned media from mesenchymal stem cells derived from a source selected from the group consisting of: placental tissue, amniotic membrane, umbilical cord tissue, fallopian tube tissue, and subepithelial umbilical cord tissue and treated with interferon gamma; d) separating T regulatory cells from said immune cell population and administering said T regulatory cells back into said patient in need of treatment; and e) administering an agent capable of enhancing the number and/or activity of myeloid suppressor cells selected from the group consisting of granulocyte-macrophage colony-stimulating factor (GM-CSF) and Bacillus Calmette-Guérin (BCG) vaccine into said patient.

2. The method of claim 1, wherein said separated T regulatory cells express FoxP3.

3. The method of claim 1, wherein said separated T regulatory cells express membrane TGF-beta.

4. The method of claim 1, wherein the conditioned media expresses at least 200 pg/ml of hepatocyte growth factor (HGF) after treatment with interferon gamma.

5. The method of claim 1, wherein said immune cell population are splenocytes.

6. The method of claim 1, wherein the T regulatory cells are administered to the patient intravenously.

7. The method of claim 1, wherein said separated T regulatory cells express membrane TGF-beta and FoxP3.

8. The method of claim 1, wherein said separated T regulatory cells express the following markers: CD4+, CD25+, and CD3+.

9. The method of claim 1, wherein said separated T regulatory cells express the following markers: CD3+, CD28+, CD4+, CD8+, CD45RA+, and CD45RO+ T cells.

10. The method of claim 1, wherein said separated T regulatory cells express the following markers: CD3+, and CD28+.

11. The method of claim 1, wherein said separated T regulatory cells express the following markers: CD4+ and CD25+.

12. The method of claim 1, wherein the mesenchymal stem cells express the following markers: CD73, CD90 and CD105 and do not express: CD14, CD45, and CD34.

13. The method of claim 1, wherein the mesenchymal stem cells express the following markers: oxidized low density lipoprotein receptor 1 b, chemokine receptor ligand 3, and granulocyte chemotactic protein and do not express CD117, CD31, CD34, and CD45.

14. The method of claim 1, wherein the mesenchymal stem cells express the following markers: CD10, CD13, C44, CD73, CD90, platelet-derived growth factor receptor-alpha (PDGFr-alpha), Programmed cell death ligand 2 (PD-L2), and human leukocyte antigens (HLA) selected from the group consisting of A, B, and C, and do not express CD31, CD34, C45, CD80, CD86, CD117, CD141, CD178, B7-H2, HLA-G and HLA, selected from the group consisting of DR, DP, and DQ.

* * * * *